(12) United States Patent
Iha et al.

(10) Patent No.: US 10,338,077 B2
(45) Date of Patent: Jul. 2, 2019

(54) METHODS FOR DETERMINING DRUG EFFICACY FOR TREATMENT OF CANCER RATION OF CEREBLON ASSOCIATED PROTEINS

(71) Applicants: Celgene Corporation, Summit, NJ (US); National University Corporation Oita University, Oita (JP)

(72) Inventors: Hidekatsu Iha, Oita (JP); Emi Ikebe, Oita (JP)

(73) Assignee: CELGENE CORPORATION, Summit, NJ (US)

( * ) Notice: Subject to any disclaimer, the term of this patent is extended or adjusted under 35 U.S.C. 154(b) by 50 days.

(21) Appl. No.: 15/170,789

(22) Filed: Jun. 1, 2016

(65) Prior Publication Data
US 2016/0356778 A1    Dec. 8, 2016

Related U.S. Application Data

(60) Provisional application No. 62/237,905, filed on Oct. 6, 2015, provisional application No. 62/170,099, filed on Jun. 2, 2015.

(51) Int. Cl.
*C12Q 1/6886* (2018.01)
*G01N 33/574* (2006.01)
*A61K 31/454* (2006.01)

(52) U.S. Cl.
CPC ..... *G01N 33/57484* (2013.01); *A61K 31/454* (2013.01); *C12Q 1/6886* (2013.01); *G01N 33/57426* (2013.01); *C12Q 2600/106* (2013.01); *C12Q 2600/158* (2013.01); *G01N 2333/47* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 9,365,640 B2 * | 6/2016 | Lopez-Girona | C07K 16/18 |
| 9,857,359 B2 | 1/2018 | Schafer et al. | |
| 10,047,151 B2 | 8/2018 | Lopez-Girona et al. | |
| 2012/0322073 A1 | 12/2012 | Lopez-Girona et al. | |
| 2014/0066480 A1 | 3/2014 | Stewart et al. | |
| 2014/0162282 A1 | 6/2014 | Schafer et al. | |
| 2016/0312292 A1 | 10/2016 | Trotter | |
| 2016/0313300 A1 | 10/2016 | Trotter et al. | |
| 2016/0319005 A1 | 11/2016 | Lopez-Girona et al. | |
| 2017/0038387 A1 | 2/2017 | Gandhi et al. | |
| 2017/0088901 A1 | 3/2017 | Trotter et al. | |
| 2017/0199193 A1 | 7/2017 | Filvaroff et al. | |
| 2017/0242014 A1 | 8/2017 | Hagner et al. | |
| 2018/0209961 A1 | 7/2018 | Schafer et al. | |
| 2018/0231561 A1 | 8/2018 | Gandhi et al. | |
| 2019/0004033 A1 | 1/2019 | Trotter et al. | |

FOREIGN PATENT DOCUMENTS

WO    WO 2017027672 A1    2/2017

OTHER PUBLICATIONS

Zhu et al (Blood, 2014, 124:536-545; published online Jun. 9, 2014).*
Uike et al (Blood, ASH Annual Meeting Abstracts, 2012, 120:abstract #2737).*
Phillips et al (Int J Blood Research Disorders, 2015, 2:1; published Mar. 21, 2015).*
Kronke et al (Science, Jan. 2014, 343:301-305).*
Lu et al (Science, Jan. 2014, 343:305-309).*
International Search Report and Written Opinion dated Sep. 14, 2016, of corresponding PCT Application No. PCT/US2016/035198 (9 pages).
Zhu et al., 2014, "Ikaros expression levels to predict response and survival following pomalidomide and dexamethasone in multiple myeloma (MM)," http://ascopubs.org/doi/abs/10.1200.jco.2014.32.15_suppl.8540, p. 8540, abstract.
Heintel et al., 2013, "High expression of cereblon (CRBN) is associated with improved clinical response in patients with multiple myeloma treated with lenalidomide and dexamethasone," British Journal of Haematology, 161(5):695-700.
Zhu et al., 2014, "Identification of cereblon-binding proteins and relationship with response and survival after IMiDs in multiple myeloma," Blood, 124(4):536-545.
Phillips et al., 2015, "International Journal of Blood Research and Disorders Lenalidomide in patients with Relapsed or Refractory HTLV-1 Related Adust T cell Leukemia/Lymphoma (ATLL)," https://clinmed journals.org/articles/ijbrd/ijbrd-2-010.pdf.
Huang et al., 2015, "Inhibition of CDK4/CDK6 Sensitizes Myeloma to IMiD by Reducing the MEIS2 to Cerblon Ratio That Accelerate IKZF1 and IKZF3 Degradation," Blood, 126(23):500, abstract.
Kinoshita et al., 2018, "Expression Levels of the Three Genes CRBN, IKZF1, and IKZF3 in Primary Multiple Myeloma Cells at Pre- and Post-Lenalidomide Treatment," https://learningcenter.ehaweb.org/eha/2018/stockholm/214993/shiori.kinoshita.expression.levels.of.the.three.genes.crbn.ikzfland.ikzf3.inhtml.
Dimopoulos et al., 2018, "Expression of CRBN, IKZF1, and IKZF3 does not predict lenalidomide sensitivity and mutations in the cereblon pathway are infrequent in multiple myeloma," Leukemia and Lymphoma, May 2, 2018, 1-9.
Supplementary European Search Report for corresponding European Application No. 16804297.6, dated Nov. 16, 2018 (13 pages).

* cited by examiner

*Primary Examiner* — Laura B Goddard
(74) *Attorney, Agent, or Firm* — Jones Day

(57) ABSTRACT

A method of identifying a subject having cancer who is likely to be responsive to a treatment compound, comprising administering a treatment compound to a subject having cancer; obtaining a sample from the subject; determining the ratio of a first biomarker level to a second biomarker level in the sample from the subject, wherein at least one of the biomarkers is a CRBN-associated protein; and diagnosing the subject as being likely to be responsive to the treatment compound if the ratio of the biomarker levels in the sample of the subject changes as compared to a reference ratio of the biomarker levels.

4 Claims, 8 Drawing Sheets

METHODS FOR DETERMINING DRUG EFFICACY FOR TREATMENT OF CANCER RATION OF CEREBLON ASSOCIATED PROTEINS

CROSS REFERENCE TO RELATED APPLICATIONS

This application claims the benefit of priority to U.S. Provisional Patent Application No. 62/170,099, filed Jun. 2, 2015, and U.S. Provisional Patent Application No. 62/237,905, filed Oct. 6, 2015, the disclosures of which are incorporated by reference herein in their entireties.

1. FIELD

Provided herein are methods for predicting the clinical sensitivity of cancer, e.g., Adult T-cell Leukemia (ATL), and a subject's response to treatment with an immunomodulatory agent, such as lenalidomide.

2. BACKGROUND

2.1 Cancer and Adult T-Cell Leukemia (ATL)

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multi-step process that begins with minor pre-neoplastic changes, which may progress to neoplasia under certain conditions. The neoplastic lesion may evolve clonally and develop an increasing capacity for invasion, growth, metastasis, and heterogeneity, especially under conditions in which the neoplastic cells escape the host's immune surveillance. Roitt et al., *Immunology*, 17.1-17.12 (3rd ed., Mosby, St. Louis, Mo., 1993).

Enormous varieties of cancer are described in details in the medical literature. Examples include cancers of the lung, gastric, colon, pancreatic, liver, rectum, prostate, breast, brain, blood, and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in blood cancer (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancer are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a, b-FGF), angiogenin, vascular endothelial growth factor (VEGF), and TNF-α. Alternatively, tumor cells can release angiogenic peptides through the production of proteases and the subsequent breakdown of the extracellular matrix where some cytokines (e.g., b-FGF) are stored. Angiogenesis can also be induced indirectly through the recruitment of inflammatory cells (particularly macrophages) and the subsequent release of angiogenic cytokines (e.g., TNF-α, b-FGF) from these inflammatory cells.

Blood cancer generally includes three main types: lymphoma, leukemia, and myeloma.

Lymphoma refers to cancer that originates in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs. Lymphoma may involve the bone marrow and the blood in some cases. Lymphoma may spread from one site to other parts of the body.

The treatments of various forms of lymphoma are described, for example, in U.S. Pat. No. 7,468,363, the entirety of which is incorporated herein by reference. Lymphoma include, but are not limited to, Hodgkin's lymphoma, non-Hodgkin's lymphoma (NHL), cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma, mantle zone lymphoma, and low grade follicular lymphoma.

Leukemia refers to malignant neoplasms of the blood-forming tissues. Various forms of leukemia are described, for example, in U.S. Pat. No. 7,393,862 and U.S. Provisional Patent Application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17th ed. 1999). Transformation to malignancy typically occurs in a single cell through two or more steps with subsequent proliferation and clonal expansion. In some leukemia, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemia involves predominantly undifferentiated cell populations, whereas chronic leukemia involves more mature cell forms.

Acute leukemia is divided into acute lymphoblastic leukemia (ALL) and acute non-lymphoblastic leukemia (ANLL) types. *The Merck Manual*, 946-949 (17th ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myeloid leukemia (AML), acute myelogenous leukemia, acute myeloblastic leukemia, acute myelocytic leukemia, or acute graulocytic leukemia, occurs at all ages and is the more common acute leukemia among adults; it is the form usually associated with irradiation as a causative agent.

Chronic leukemia is divided into chronic lymphocytic leukemia (CLL) or chronic myelocytic leukemia (CML). *The Merck Manual*, 949-952 (17th ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. For CIVIL, the characteristic feature is the predominance of granulocytic cells of all stages of differentiation in blood, bone marrow, liver, spleen, and other organs. In symptomatic CML patients, the total white blood cell (WBC) count is usually about 200,000/µL, but may reach 1,000,000/µL at diagnosis. CIVIL is relatively easy to diagnose because of the presence of the Philadelphia chromosome.

Myeloma is a cancer of plasma cells in the bone marrow. Normally, plasma cells produce antibodies and play a key role in immune function. However, uncontrolled growth of these cells leads to bone pain and fractures, anemia, infections, and other complications. Because myeloma frequently occurs at many sites in the bone marrow, it is often referred to as multiple myeloma. multiple myeloma is the second most common hematological malignancy, although the exact causes of multiple myeloma remain unknown. multiple myeloma causes high levels of proteins, including but not limited to, M-protein and other immunoglobulins (antibodies), albumin, and beta-2-microglobulin in the blood, urine, and organs. M-protein, short for monoclonal protein, also known as paraprotein, is a particularly abnormal protein produced by the myeloma plasma cells and can be found in the blood or urine of almost all patients with multiple myeloma.

Adult T-cell leukemia/lymphoma (ATL or ATLL) is a cancer of the immune system's T-cells. ATL is a rare and often aggressive (fast-growing) T-cell lymphoma that can be found in the blood (leukemia), lymph nodes (lymphoma), skin, or multiple areas of the body. ATL has been linked to infection by the human T-cell lymphotropic virus type 1 (HTLV-1). ATL is frequently accompanied by visceral involvement, hypercalcemia, skin lesions, and lytic bone lesions. One of the striking features of ATL-induced bone disease is that the bone lesions are predominantly osteolytic with little associated osteoblastic activity. In patients with ATL, elevated serum levels of IL-1, TGF-β, PTHrP, macrophage inflammatory protein (MIP-1α), and receptor activator of NF-κB ligand (RANKL) have been associated with hypercalcemia. See the website of Lymphoma Research Foundation.

There are four subtypes of ATL: acute, lymphomatous, chronic, and smoldering. Acute and lymphomatous ATL are fast-growing forms of ATL, whereas chronic and smoldering ATL are less aggressive. Symptoms of acute ATL usually develop rapidly and may include fatigue, skin rash, and enlarged lymph nodes in the neck, underarm, or groin. Acute ATL usually associates with a high white blood cell count accompanied by an elevated level of calcium in the blood (hypercalcemia). Lymphomatous ATL also develops rapidly and is usually found in the lymph nodes but may also cause high white blood cell counts. Chronic and smoldering ATL are less aggressive. Chronic ATL grows relatively slow and can result in elevated lymphocytes in the blood, enlarged lymph nodes, skin rash, or fatigue. Smoldering ATL is usually associated with very mild symptoms, such as a few skin lesions. See Id.

Till now, there have not been sufficient clinical trials to establish treatment standards for ATL in the United States and Europe, especially for the acute and lymphomatous subtypes. As a result, common first-line therapies used to treat ATL are the same as those used to treat other types of T-cell lymphomas, such as CHOP (cyclophosphamide, doxorubicin, vincristine, and prednisone). Similar to the first-line setting, standard treatment for relapsed (disease returns after treatment) ATL has not been established. Many regimens used to treat other T-cell lymphomas following relapse are also being used to treat ATL. See Id.

There exists a significant need for safe and effective methods of treating, preventing, and managing cancer, e.g., ATL, particularly for cancer that is refractory to standard treatments, such as surgery, radiation therapy, chemotherapy, and hormonal therapy, while reducing or avoiding the toxicities and/or side effects associated with the conventional therapies. The present invention satisfies these and other needs.

2.2 Cereblon

At least two isoforms of the protein cereblon (CRBN) exist, which are 442 and 441 amino acids long, respectively, and CRBN is conserved from plant to human. In humans, the CRBN gene has been identified as a candidate gene of an autosomal recessive nonsyndromic mental retardation (ARNSMR). See Higgins et al., *Neurology* 2004, 63:1927-1931. CRBN was initially characterized as a "regulator of G-protein signaling" (RGS) domain-containing novel protein that interacted with a calcium-activated potassium channel protein (SLO1) in the rat brain, and was later shown to interact with a voltage-gated chloride channel (ClC-2) in the retina with AMPK1 and DDB1. See Jo et al., *J. Neurochem.* 2005, 94:1212-1224; Hohberger et al., *FEBS Lett.* 2009, 583:633-637; Angers et al., *Nature* 2006, 443:590-593. Damaged DNA-binding protein 1 (DDB1) was originally identified as a nucleotide excision repair protein that associates with damaged DNA-binding protein 2 (DDB2). Its defective activity causes the repair defect in patients with xeroderma pigmentosum complementation group E (XPE). DDB1 also appears to function as a component of numerous distinct DCX (DDB1-CUL4-X-box) E3 ubiquitin-protein ligase complexes, which mediate the ubiquitination and subsequent proteasomal degradation of target proteins. CRBN has also been identified as a target for the development of therapeutic agents for diseases of the cerebral cortex. See WO 2010/137547 A1.

CRBN has recently been identified as a key molecular target that binds to thalidomide to cause birth defects. See Ito et al., *Science* 2010, 327:1345-1350. DDB1 was found to interact with CRBN and, thus, was indirectly associated with thalidomide. Moreover, thalidomide was able to inhibit auto-ubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A, were both defective for thalidomide binding, with the double mutant having the lowest thalidomide-binding activity. Id. A link between CRBN and the teratogenic effect of thalidomide was confirmed in animal models of zebra-fish and chick embryos. Id.

It is yet to be established whether binding of thalidomide or other drugs to CRBN, the CRBN E3 ubiquitin-ligase complex, or one or more substrates of CRBN, is required for the beneficial effects of these drugs. Understanding the interactions between these drugs and CRBN or CRBN-associated proteins will facilitate elucidating molecular mechanisms of drug efficacy and/or toxicity and may lead to development of new drugs with improved efficacy and toxicity profiles.

2.3 Compounds

A number of studies have been conducted with the aim of providing immunomodulatory compounds that can safely and effectively be used to treat diseases associated with abnormal production of TNF-α. See, e.g., Marriott et al., *Expert Opin. Biol. Ther.* 2001, 1(4):1-8; Muller et al., *J. Med. Chem.* 1996, 39(17):3238-3240; Muller et al., *Bioorg. & Med. Chem. Lett.* 1998, 8:2669-2674. Some studies have focused on a group of immunomodulatory compounds selected for their capacity to potently inhibit TNF-α production by LPS-stimulated PBMC. Corral et al., *Ann. Rheum. Dis.* 1999, 58(Suppl I):1107-1113. These compounds show not only potent inhibition of TNF-α but also marked inhibition of LPS-induced monocyte production of IL-1β and IL-12. LPS-induced IL-6 is also inhibited by such compounds, albeit partially. Further, these compounds are potent stimulators of LPS-induced production of IL-10, an anti-inflamatory cytokine. Id.

Compounds for the methods provided herein include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471. Still other specific compounds disclosed herein belong to a class of isoindole-imides disclosed in U.S. Pat. Nos. 6,395,754, 6,555,554, 7,091,353, U.S. Publication No. 2004/0029832, and International Publication No. WO 98/54170, each of which is incorporated herein by reference.

Thalidomide, lenalidomide, and pomalidomide have elicited remarkable responses in patients with multiple myeloma, lymphoma, and other hematological diseases such as myelodysplastic syndrome. See Galustian et al., *Expert Opin. Pharmacother.* 2009, 10:125-133. These treatment compounds display a broad spectrum of activity, including anti-angiogenic properties, modulation of pro-inflammatory cytokines, co-stimulation of T cells, increased NK cell toxicity, direct anti-tumor effects, and modulation of stem cell differentiation.

For example, thalidomide and lenalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide may also be administered in combination with dexamethasone. U.S. Patent Application Publication No. 2004/0029832 A1, the disclosure of which is hereby incorporated in its entirety, discloses the treatment of multiple myeloma.

Another compound provided herein is 3-(5-amino-2-methyl-4-oxo-4H-quinazolin-3-yl)-piperidine-2,6-dione ("Compound A"), or an enantiomer or a mixture of enantiomers thereof, or a pharmaceutically acceptable salt, solvate, hydrate, co-crystal, clathrate, or polymorph thereof. Compound A can be prepared as described in U.S. Pat. No. 7,635,700, the disclosure of which is incorporated herein by reference in its entirety. Compound A can also be synthesized according to other methods apparent to those of skill in the art based upon the teaching herein. In certain embodiments, Compound A is in a crystalline form described in U.S. Provisional Application No. 61/451,806, filed Mar. 11, 2011, which is incorporated herein by reference in its entirety. In some embodiments, the hydrochloride salt of Compound A is used in the methods provided herein. Methods of treating, preventing, and/or managing cancer and other diseases using Compound A are described in U.S. Provisional Application No. 61/451,995, filed Mar. 11, 2011, which is incorporated herein by reference in its entirety.

Yet another compound provided herein is 3-[4-(4-Morpholin-4-ylmethyl-benzyloxy)-1-oxo-1,3-dihydro-isoindol-2-yl]-piperidine-2,6-dione ("Compound B"), or an enantiomer or a mixture of enantiomers thereof, or a pharmaceutically acceptable salt, solvate, hydrate, co-crystal, clathrate, or polymorph thereof.

The conventional methods of assessing the effects of immunomodulatory compounds require live cellular assays or lengthy clinical endpoints. These cellular tests are cumbersome and often require the use of various stimulants (e.g., LPS or anti-CD3 antibody). Indirect endpoints such as cytokine production are evaluated, which can be influenced via multiple pathways. Further, clinical efficacy of these compounds could not be correctly predicted, as it could only be measured in terms of patient response, which usually requires a minimum of several months of treatment. In view of the deficiencies of the conventional methods, there is a need to develop an efficient, sensitive, and accurate method to detect, quantify, and characterize the pharmacodynamic activity of immunomodulatory compounds.

3. SUMMARY OF THE INVENTION

In one aspect, provided herein is a method of identifying a subject having a cancer who is likely to be responsive to a treatment compound, comprising:

(a) obtaining a sample from the subject (b) determining the ratio of a first biomarker level to a second biomarker level in the sample from the subject, wherein at least one of the biomarkers is a CRBN-associated protein; and (c) diagnosing the subject as being likely to be responsive to the treatment compound if the ratio of the biomarker levels in the sample of the subject is different from a reference ratio of the biomarker levels.

In another aspect, provided herein is a method of predicting the responsiveness of a subject having or suspected of having a cancer to a treatment compound, comprising:

(a) obtaining a sample from the subject;

(b) determining the ratio of a first biomarker level to a second biomarker level in the sample from the subject, wherein at least one of the biomarkers is a CRBN-associated protein;

(c) diagnosing the subject as being likely to be responsive to a treatment of the cancer with the treatment compound if the ratio of the biomarker levels in the sample is different from the ratio of the biomarker levels obtained from a reference sample.

In some embodiments, the methods provided herein further comprise administering a therapeutically effective amount of the treatment compound to the subject diagnosed to be likely to be responsive to the treatment compound.

In another aspect, provided herein is a method of treating a cancer, comprising:

(a) obtaining a sample from a subject having a cancer;

(b) determining the ratio of a first biomarker level to a second biomarker level in the sample from the subject, wherein at least one of the biomarkers is a CRBN-associated protein;

(c) diagnosing the subject as being likely to be responsive to a treatment compound if the ratio of the biomarker levels in the sample of the subject is different from a reference ratio of the biomarker levels; and (d) administering a therapeutically effective amount of the treatment compound to the subject diagnosed to be likely to be responsive to the treatment compound.

In some embodiments, in step (c) diagnosing the subject as being likely to be responsive to a treatment compound if the ratio of the biomarker levels in the sample of the subject is higher than a reference ratio of the biomarker levels. In other embodiments, in step (c) diagnosing the subject as being likely to be responsive to a treatment compound if the ratio of the biomarker levels in the sample of the subject is lower than a reference ratio of the biomarker levels.

In yet another aspect, provided herein is a method of monitoring the efficacy of a treatment of a cancer in a subject with a treatment compound, comprising:

(a) administering a treatment compound to a subject having a cancer;

(b) obtaining a sample from the subject;

(c) determining the ratio of a first biomarker level to a second biomarker level in the sample from the subject, wherein at least one of the biomarkers is a CRBN-associated protein; and (d) comparing the ratio of the biomarker levels in the sample with the ratio of the biomarker levels obtained from a reference sample, wherein a change in the ratio as compared to the reference is indicative of the efficacy of the treatment compound in treating the cancer in the subject.

In some embodiments, an increased ratio as compared to the reference is indicative of the efficacy of the treatment compound in treating the cancer in the subject. In other embodiments, a decreased ratio as compared to the reference is indicative of the efficacy of the treatment compound in treating the cancer in the subject.

In some embodiments, the reference is prepared by using a control sample obtained from the subject having a cancer but not responsive to the compound treatment; and wherein the control sample is from the same source as the sample. In other embodiments, the reference is prepared by using a control sample obtained from a healthy subject not having the cancer; and wherein the control sample is from the same source as the sample.

In some embodiments, the cancer is a leukemia. In some embodiments, the cancer is a lymphoma. In other embodiments, the cancer is an Adult T-cell Leukemia (ATL). In other embodiments, the cancer is relapsed, refractory or resistant to conventional therapy. In other embodiments, the cancer is a relapsed or refracted ATL.

In some embodiments, the treatment compound is an immunomodulatory compound. In some embodiments, the treatment compound is lenalidomide.

In a specific embodiment, the treatment compound is lenalidomide and the cancer is ATL.

In some embodiments, the first biomarker is selected from the group comprising CRBN, IKZF1, and IKZF2. In some embodiments, the second biomarker is selected from the group comprising CRBN, IKZF1, and IKZF2. In some embodiments, the first biomarker and the second biomarker are selected from the group comprising CRBN, IKZF1, and IKZF2, and wherein the ratio of the biomarker levels changes as compared to a reference.

In some embodiments, the ratio of the biomarker levels increases as compared to a reference. In other embodiments, the ratio of the biomarker levels decreases as compared to a reference.

In some embodiments, the first biomarker is CRBN. In some embodiments, when the first biomarker is CRBN, the second biomarker is a substrate of CRBN. In other embodiments, when the first biomarker is CRBN, the second biomarker is not a substrate of CRBN.

In some embodiments, the first biomarker is CRBN and the second biomarker is IKZF1. In some embodiments, the ratio of the CRBN expression level to the IKZF1 expression level is higher than 3. In other embodiments, the ratio of the CRBN expression level to the IKZF1 expression level is higher than 4. In yet other embodiments, the ratio of the CRBN expression level to the IKZF1 expression level is higher than 5.

In other embodiments, the first biomarker is CRBN and the second biomarker is IKZF2. In some embodiments, the ratio of the CRBN expression level to the IKZF2 expression level is between 500 and 5000. In other embodiments, the ratio of the CRBN expression level to the IKZF2 expression level is higher than 500. In other embodiments, the ratio of the CRBN expression level to the IKZF2 expression level is higher than 1000. In yet other embodiments, the ratio of the CRBN expression level to the IKZF2 expression level is higher than 1500. In yet other embodiments, the ratio of the CRBN expression level to the IKZF2 expression level is higher than 2500.

In some embodiments, the level of the biomarker is measured by determining the protein level of the biomarker. In some embodiments, the methods provided herein comprise contacting proteins within the sample with a first antibody that immunospecifically binds to the biomarker protein. In some embodiments, the methods provided herein further comprise:

(i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody;

(ii) detecting the presence of the second antibody bound to the proteins; and (iii) determining the amount of the biomarker protein based on the amount of the detectable label in the second antibody.

In other embodiments, the methods provided herein further comprise:

(i) contacting the biomarker protein bound to the first antibody with a second antibody with a detectable label, wherein the second antibody immunospecifically binds to the first antibody;

(ii) detecting the presence of the second antibody bound to the proteins; and (iii) determining the amount of the biomarker protein based on the amount of the detectable label in the second antibody.

In other embodiments, the level of the biomarker is measured by determining the mRNA level of the biomarker. In yet other embodiments, the level of the biomarker is measured by determining the cDNA level of the biomarker. In some embodiments, the level of the biomarker is measured using quantative PCR (qPCR).

4. BRIEF DESCRIPTION OF THE FIGURES

Figure 3:
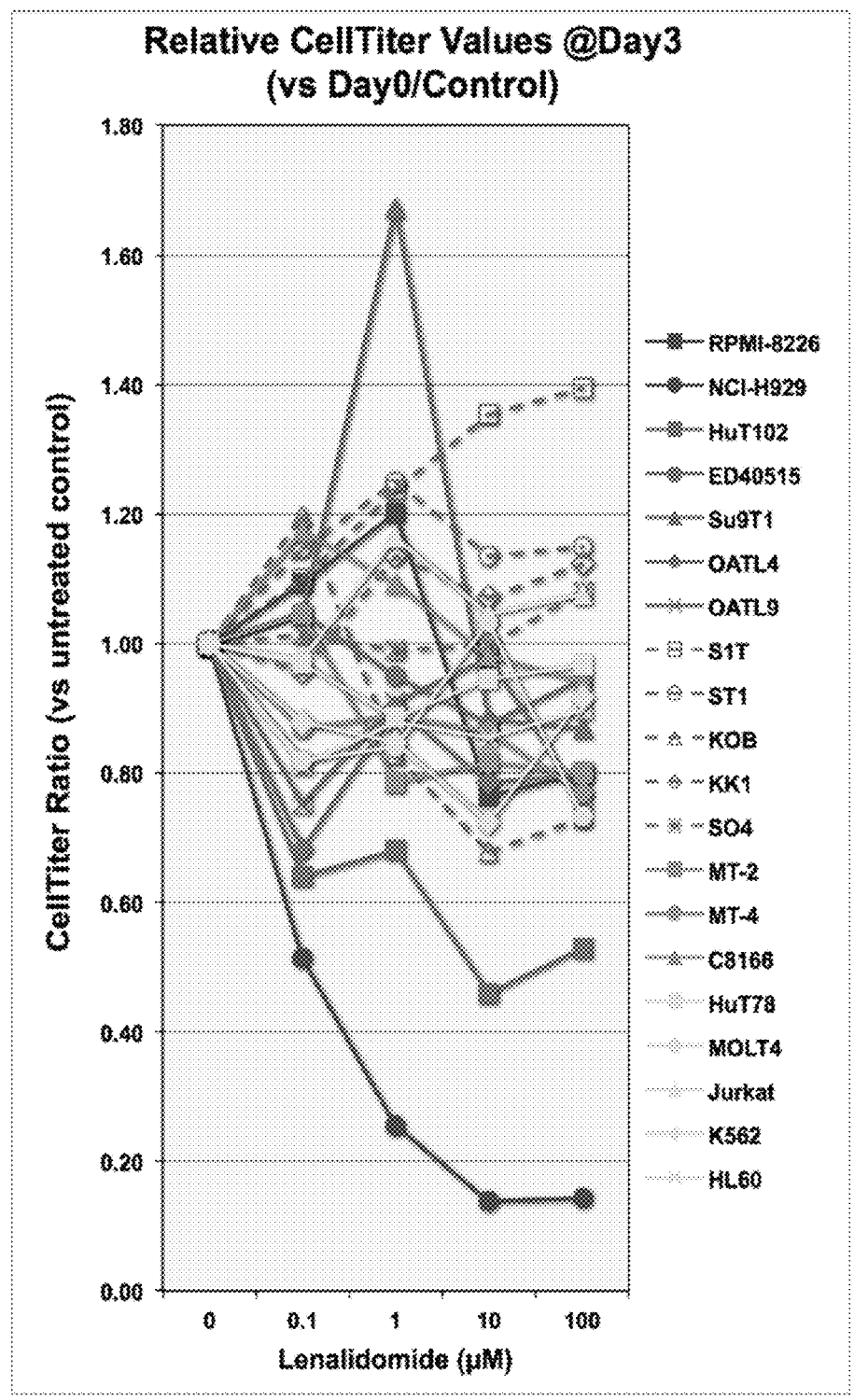

FIG. 3 demonstrates various proliferation inhibitory effects of lenalidomide on different types of cells, including two control multiple myeloma cells, ten ATL cells, three HTLV-1-transformed cells, and five non-ATL cells.

Figure 4:
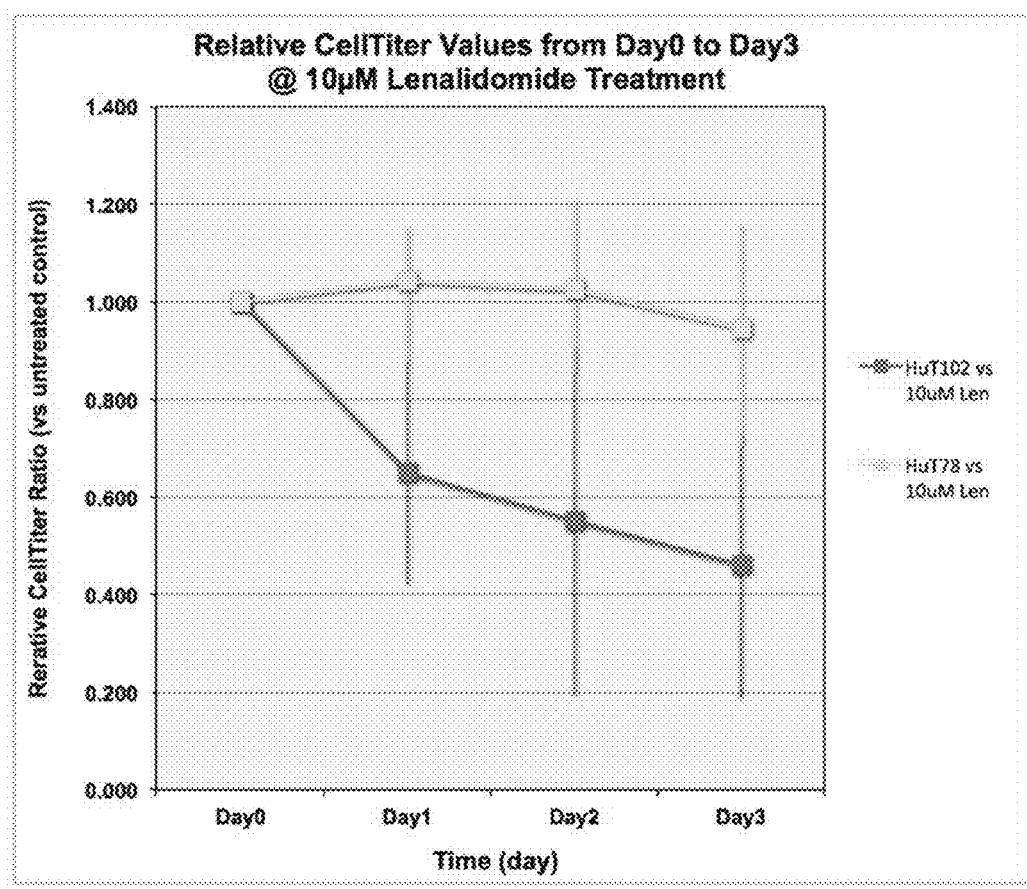

FIG. 4 demonstrates time-dependent cell growth inhibition by lenalidomide.

Figure 5A:
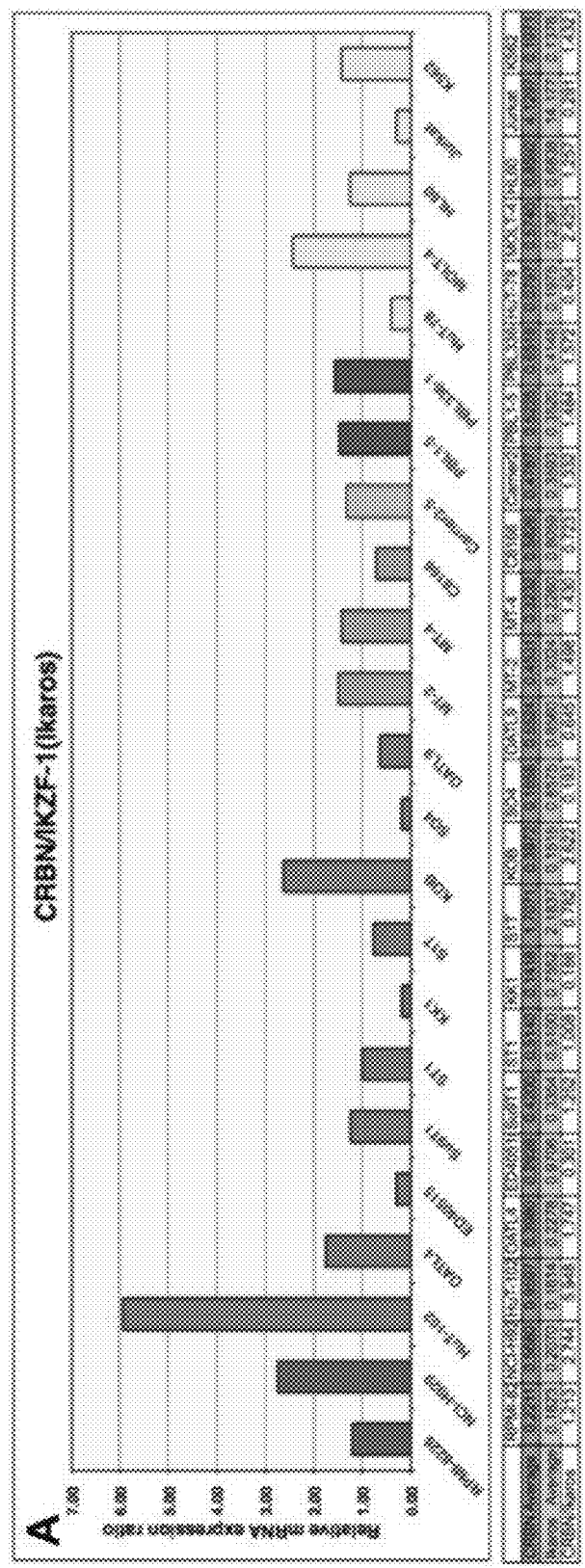
Figure 5B:
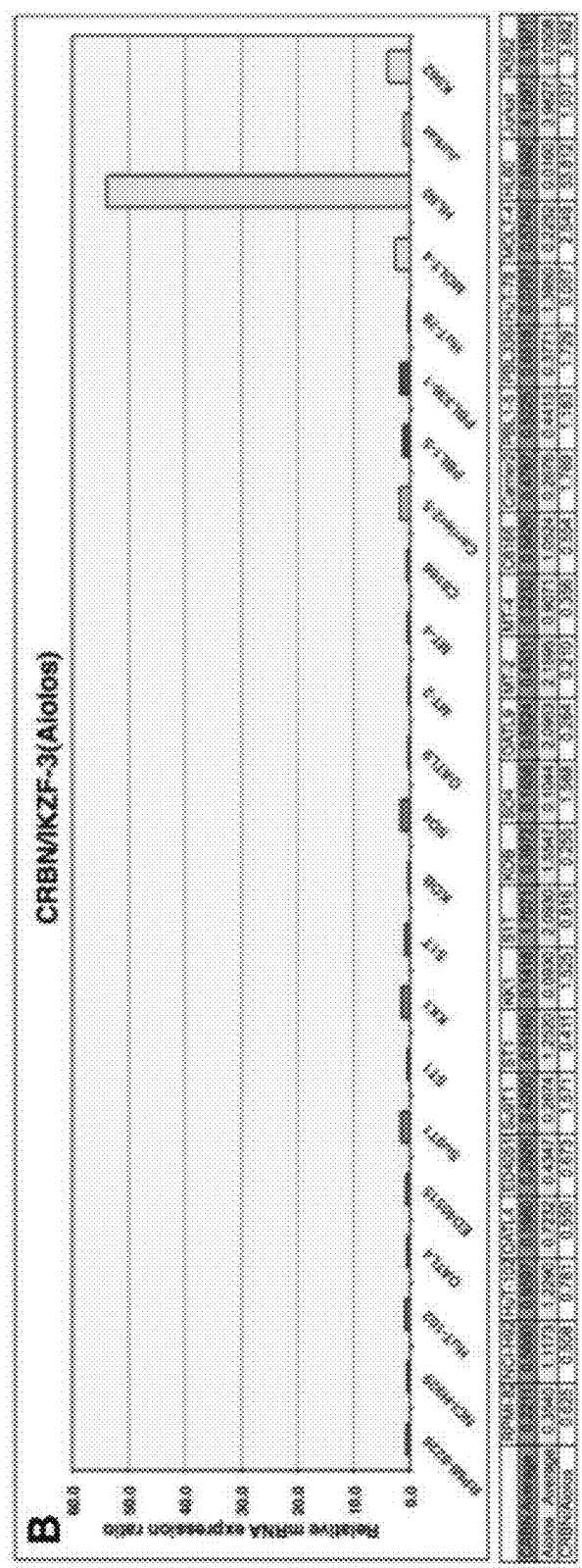
Figure 5C:
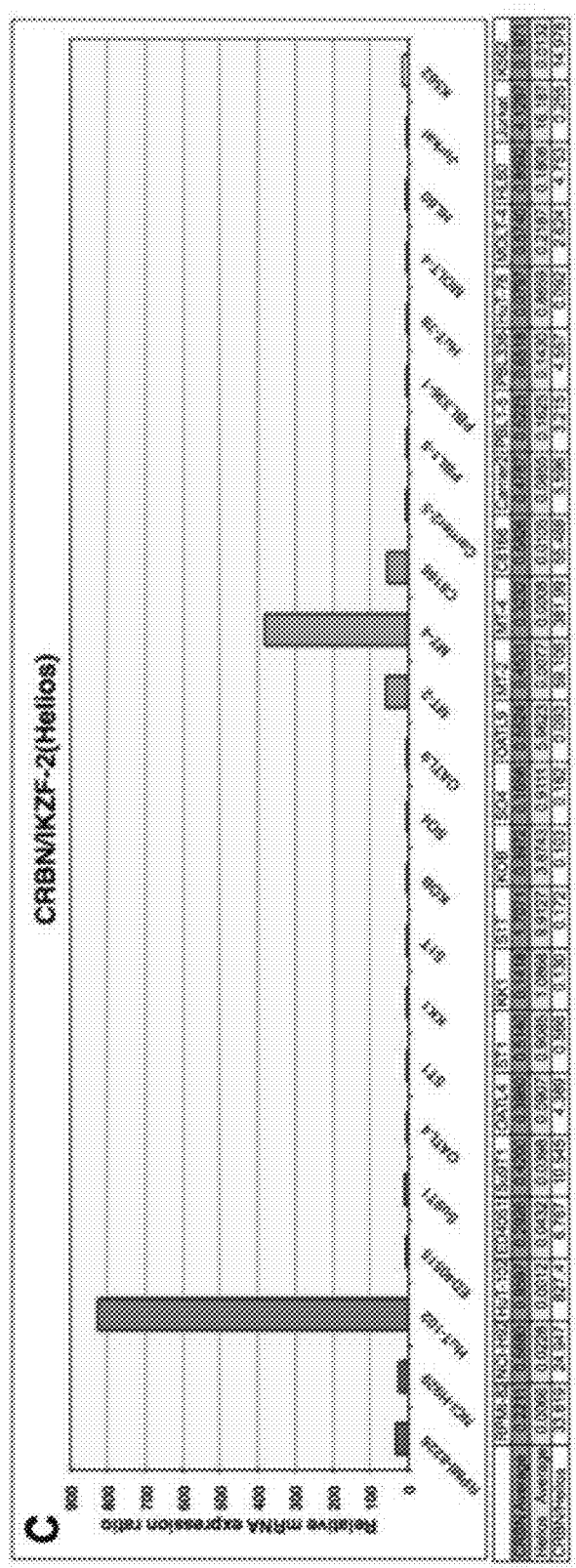

FIGS. 5A-5C show the ratios of mRNA expression levels of CRBN to IKZF1 (FIG. 5A), CRBN to IKZF3 (FIG. 5B), and CRBN to IKZF2 (FIG. 5C) in different types of cells.

Figure 6:
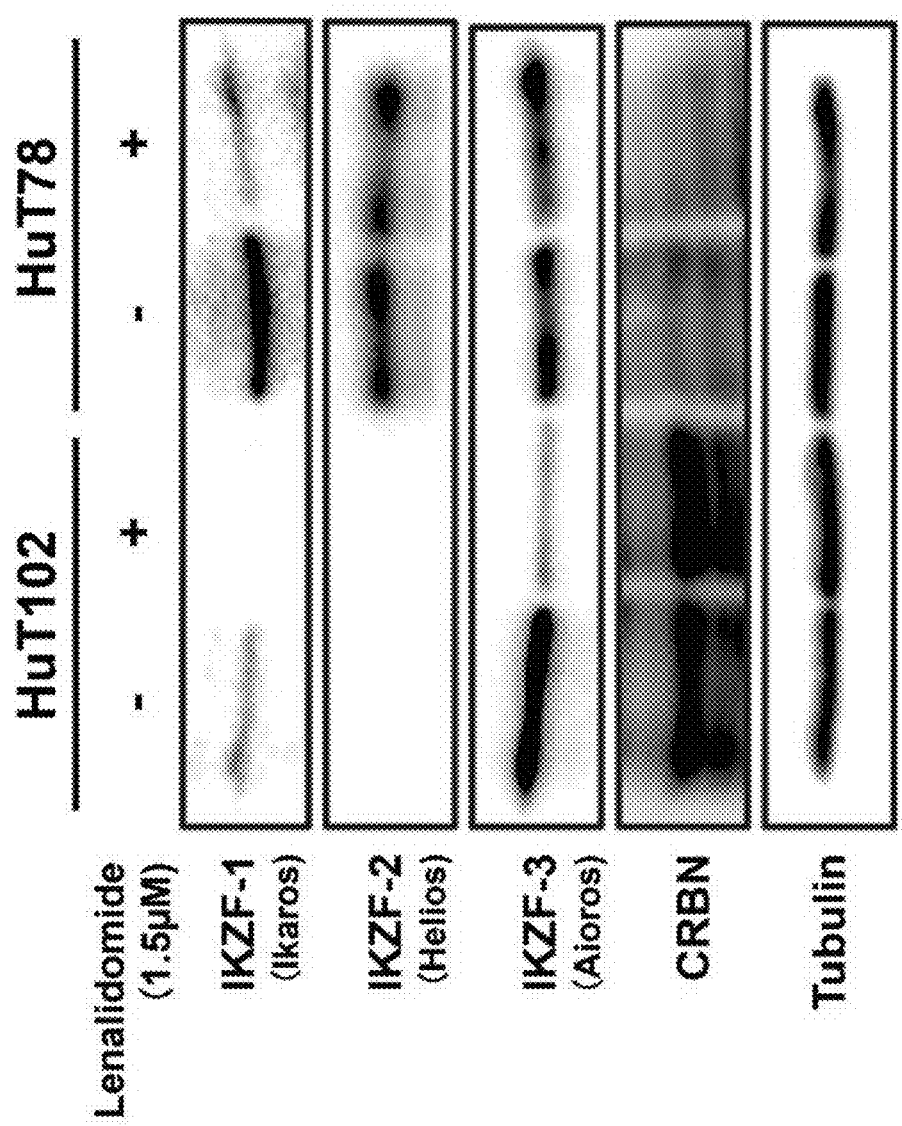

FIG. 6 demonstrates lenalidomide-induced degradation of IKZF family proteins in lenalidomide-sensitive ATL cell line HuT102.

5. DETAILED DESCRIPTION OF THE INVENTION

The methods provided herein are based, in part, on the finding that the ratio of the expression level of CRBN to another protein correlates with an ATL patient's responsiveness to treatment with an immunomodulatory compound, e.g., lenalidomide. For example, as shown in Sections 6.2 and 6.5, lenalidomide-responsive ATL cell lines have higher ratio of the mRNA expression level of CRBN to IKZF1 and CRBN to IKZF2 as compared with non-responsivie ATL cell lines and other cell lines.

The methods provided herein are also based, in part, on the finding that the expression level of certain CRBN-associated protein correlates with an ATL patient's responsiveness to treatment with an immunomodulatory compound, e.g., lenalidomide. For example, as shown in Section 6.5, lenalidomide-responsive ATL cell lines have extremely low mRNA expression level of IKZF2.

Three members of the IKAROS protein family (Ikaros, Helios, and Aiolos) are hematopoietic-specific transcription factors involved in the regulation of lymphocyte development. They all belong to the zinc-finger DNA-binding proteins associated with chromatin remodeling.

IKZF1 (IKAROS zinc finger 1; also called Ikaros) is expressed restrictively to the fetal and adult hemo-lymphopoietic system, and it functions as a regulator of lymphocyte differentiation. Several alternatively spliced transcript variants encoding different isoforms have been described for this gene. All isoforms share a common C-terminal domain, which contains two zinc finger motifs that are required for hetero- or homo-dimerization and for interactions with other proteins. The isoforms, however, differ in the number of N-terminal zinc finger motifs that bind DNA and contain the nuclear localization signal, resulting in members with and without DNA-binding properties. Only few isoforms contain the requisite three or more N-terminal zinc motifs that confer high affinity binding to a specific core DNA sequence element in the promoters of target genes. The non-DNA-binding isoforms are largely found in the cytoplasm, and thought to function as dominant negative factors. Overexpression of some dominant-negative isoforms have been associated with B-cell malignancies, such as acute lymphoblastic leukemia (ALL).

IKZF2 (IKAROS zinc finger 2; also called Helios) forms homo- or hetero-dimers with other Ikaros family members, and is thought to function predominantly in early hematopoietic development.

IKZF3 (IKAROS zinc finger 3; also called Aiolos) is a transcription factor that is important in the regulation of B lymphocyte proliferation and differentiation. Both Ikaros and Aiolos can participate in chromatin remodeling. Regulation of gene expression in B lymphocytes by Aiolos is complex as it appears to require the sequential formation of Ikaros homodimers, Ikaros/Aiolos heterodimers, and Aiolos homodimers.

Figure 1:
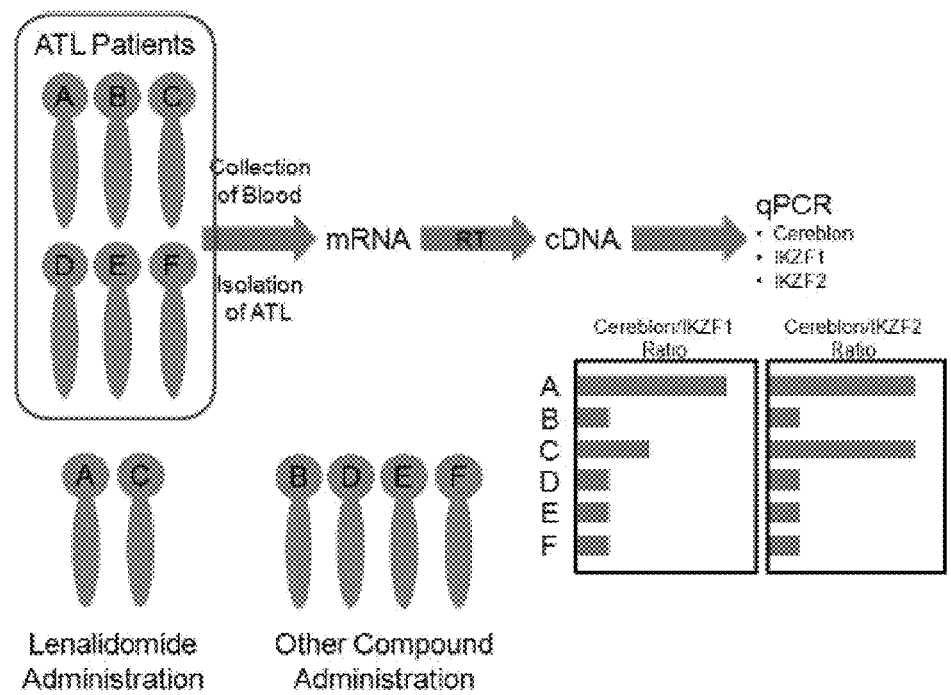
FIG. 1 illustrates an embodiment of the present method for determining ATL patients who are sensitive or responsive to lenalidomide.

Thus, in certain embodiments, the ratio of CRBN to IKZF1 and/or CRBN to IKZF2 can be used to select lenalidomide-responsive ATL patients, or to predict an ATL patient's responsiveness to treatment with lenalidomide. For example, in one embodiment as shown in FIG. 1, ATL tissues or cells can first be isolated from the patient; RNA (total RNA or mRNA) of CRBN, IKZF1, and IKZF2 can then be extracted and quantitated; the ratio of CRBN/IKZF1 and/or CRBN/IKZF2 can be calculated. Based on the above ratios, a patient showing higher CRBN/IKZF1 and/or CRBN/IKZF2 ratio can be administered with lenalidomide. In some embodiments, cells are isolated with magnetic beads attached with anti-CD4 and anti-CD25 antibodies. The population of HTLV-1 positive cells are calculated using RT-PCR analysis on pX region of HTLV-1 provirus.

In other embodiments, the mRNA expression level of IKZF2 can be used to select lenalidomide-responsive ATL patients, or to predict an ATL patient's responsiveness to treatment with lenalidomide.

5.1 DEFINITIONS

As used herein, and unless otherwise specified, the terms "treat," "treating," and "treatment" refer to an action that occurs while a patient is suffering from the specified cancer, which reduces the severity of the cancer, or retards or slows the progression of the cancer.

The term "sensitivity" or "sensitive" when made in reference to treatment with a compound is a relative term, which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least 5%, or more, in the effectiveness of the compound treatment.

As used herein, the term "cereblon-associated protein" or "CAP" refers to cereblon (CRBN) itself or a protein that interacts with or binds to CRBN, either directly or indirectly. For example, the term refers to any protein that directly binds to CRBN, as well as any protein that is an indirect downstream effector of CRBN pathways. In certain embodiments, a "cereblon-associated protein" or "CAP" is a substrate of CRBN, for example, a protein substrate of the E3 ubiquitin ligase complex involving CRBN, or the downstream substrates thereof. In one embodiment, the CAP provided herein is a substrate of CRBN such as IKZF1, also known as "Ikaros." In another embodiment, the CAP provided herein is a substrate of CRBN such as IKZF2, also known as "Helios." In yet another embodiment, the CAP provided herein is a substrate of CRBN such as IKZF3, also known as "Aiolos." In certain embodiments, a "cereblon-associated protein" or "CAP" is a binding protein of CRBN.

As used herein, the terms "compound" and "treatment compound" are used interchangeably and include immunomodulatory compounds or immunomodulatory drugs. As used herein, the term "immunomodulatory compound" or "immunomodulatory drug" refers generally to a molecule or agent capable of altering the immune response in some way. Non-limiting examples of immunomodulatory compounds include those disclosed in Section 5.6 below.

As used herein, and unless otherwise specified, the term "therapeutically effective amount" of a compound is an amount sufficient to provide a therapeutic benefit in the treatment or management of cancer, or to delay or minimize one or more symptoms associated with the presence of cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to treatment refers to the degree of effectiveness of the treatment in lessening or decreasing the symptoms of a disease, e.g., ATL, being treated. For example, the term "increased responsiveness" when used in reference to treatment of a cell or a subject refers to an increase in the effectiveness of the treatment in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

As used herein, the term "effective subject response," "effective patient response," or "effective patient tumor response" refers to any increase in the therapeutic benefit to the patient. An "effective patient tumor response" can be, for example, about 5%, about 10%, about 25%, about 50%, or about 100% decrease in the progress rate of the tumor. An "effective patient tumor response" can be, for example, about 5%, about 10%, about 25%, about 50%, or about 100% decrease in the physical symptoms of the tumor. An "effective patient tumor response" can also be, for example, about 5%, about 10%, about 25%, about 50%, about 100%, about 200%, or more increase in the response of the patient, as measured by any suitable means, such as gene expression, cell counts, assay results, tumor size, etc.

An improvement in cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, at least about 20%, at least about 30%, at least about 40%, at least about 50%, at least about 60%, at least about 70%, at least about 80%, or at least about 90% decrease in all measurable tumor burden (i.e., the number of malignant cells present in the subject, the measured bulk of tumor masses, or the quantity of abnormal monoclonal protein) in the absence of new lesions. The term "treatment" contemplates both a complete and a partial response.

The term "likelihood" or "likely" generally refers to an increase in the probability of an event. The term "likelihood" or "likely" when used in reference to the effectiveness of a patient tumor response generally contemplates an increased probability that the rate of tumor progress or tumor cell growth will decrease. The term "likelihood" or "likely" when used in reference to the effectiveness of a patient tumor response can also generally mean the increase of indicators, such as mRNA or protein expression, that may evidence an increase in the progress in treating the tumor.

The term "predict" generally means to determine or to tell in advance. When used to "predict" the effectiveness of cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating cancer in a patient or in a tumor cell culture. Similarly, the term "monitoring," when used in connection with patient compliance, either individually or in a clinical trial, refers to the tracking or confirming that the patient is actually taking a drug being tested as prescribed. The monitoring can be performed, for example, by following the mRNA or protein expression of biomarkers.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The term "regulate" as used herein refers to controlling the activity of a molecule or biological function, such as enhancing or diminishing the activity or function.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma, and leukemia), and solid tumors.

The term "refractory or resistant" refers to a circumstance where patients, even after intensive treatment, have residual cancer cells (e.g., lymphoma cells) in their lymphatic system, blood, and/or blood forming tissues (e.g., bone marrow).

A "biological marker" or "biomarker" is a substance whose detection indicates a particular biological state, such as, for example, the presence of cancer. In some embodiments, biomarkers can be determined individually. In other embodiments, several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as mRNA or cDNA.

In additional embodiments, a "biomarker" indicates a change in the level of polypeptide or protein expression that may correlate with the risk or progression of a disease, or patient's susceptibility to treatment. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

The terms "polypeptide" and "protein" as used interchangeably herein refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived or synthetic. The polypeptide can be purified from a biological sample. The polypeptide, protein, or peptide also encompasses modified polypeptides, proteins, and peptides, e.g., a glycopolypeptide, glycoprotein, or glycopeptide; or a lipopolypeptide, lipoprotein, or lipopeptide.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4).

The terms "antigen binding domain," "antigen binding region," "antigen binding fragment," and similar terms refer to the portion of an antibody that comprises the amino acid residues that interact with an antigen and confer on the binding agent its specificity and affinity for the antigen (e.g., the CDR). The antigen binding region can be derived from any animal species, such as rodents (e.g., rabbit, rat, or hamster) and humans. In some embodiments, the antigen binding region is of human origin.

The term "constant region" or "constant domain" of an antibody refers to a carboxy terminal portion of the light and heavy chain that is not directly involved in binding of the antibody to antigen but exhibits various effector functions, such as interaction with the Fc receptor. The term refers to the portion of an immunoglobulin molecule that has a more conserved amino acid sequence relative to the other portion of the immunoglobulin, the variable domain, which contains the antigen binding site. The constant domain contains CH1, CH2 and CH3 domains of the heavy chain and the CL domain of the light chain.

The term "epitope" as used herein refers to a localized region on the surface of an antigen that is capable of binding to one or more antigen binding regions of an antibody, that has antigenic or immunogenic activity in an animal, such as a mammal (e.g., a human), and that is capable of eliciting an immune response. An epitope having immunogenic activity is a portion of a polypeptide that elicits an antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules, such as amino acids or sugar side chains, and have specific three dimensional structural characteristics as well as specific charge characteristics. A region of a polypeptide contributing to an epitope may be contiguous amino acids of the polypeptide, or the epitope may come together from two or more non-contiguous regions of the polypeptide. The epitope may or may not be a three-dimensional surface feature of the antigen.

The terms "fully human antibody" and "human antibody" are used interchangeably herein and refer to an antibody that comprises a human variable region and, in some embodiments, a human constant region. In specific embodiments, the terms refer to an antibody that comprises a variable region and a constant region of human origin. The term "fully human antibody" includes antibodies having variable and constant regions corresponding to human germline immunoglobulin sequences as described by Kabat et al., *Sequences of Proteins of Immunological Interest*, U.S. Department of Health and Human Services, NIH Publication No. 91-3242 (5th ed. 1991).

The phrase "recombinant human antibody" includes human antibodies that are prepared, expressed, created, or isolated by recombinant means, such as antibodies expressed using a recombinant expression vector transfected into a host cell, antibodies isolated from a recombinant, combinatorial human antibody library, antibodies isolated from an animal (e.g., a mouse or a cow) that is transgenic and/or transchromosomal for human immunoglobulin genes (see, e.g., Taylor et al., *Nucl. Acids Res.* 1992, 20:6287-6295) or antibodies prepared, expressed, created, or isolated by any other means that involves splicing of human immunoglobulin gene sequences to other DNA sequences. Such recombinant human antibodies can have variable and constant regions derived from human germline immunoglobulin sequences. See Kabat et al., *Sequences of Proteins of Immunological Interest*, U.S. Department of Health and Human Services, NIH Publication No. 91-3242 (5th ed. 1991). In certain embodiments, however, such recombinant human antibodies are subjected to in vitro mutagenesis (or, when an animal transgenic for human Ig sequences is used, in vivo somatic mutagenesis) and thus the amino acid sequences of the heavy chain variable and light chain variable regions of the recombinant antibodies are sequences that, while derived from and related to human germline heavy chain variable and light chain variable sequences, may not naturally exist within the human antibody germline repertoire in vivo.

The term "heavy chain" when used in reference to an antibody refers to five distinct types, called alpha ($\alpha$), delta ($\delta$), epsilon ($\epsilon$), gamma ($\gamma$) and mu ($\mu$), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. In some embodiments the heavy chain is a human heavy chain.

The term "Kabat numbering" and similar terms are recognized in the art and refer to a system of numbering amino acid residues that are more variable (i.e., hypervariable) than other amino acid residues in the heavy and light chain variable regions of an antibody, or an antigen binding portion thereof. Kabat et al., *Ann. NY Acad. Sci.* 1971, 190:382-391; Kabat et al., *Sequences of Proteins of Immunological Interest*, U.S. Department of Health and Human Services, NIH Publication No. 91-3242 (5th ed. 1991). For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3. Other numbering schemes will be readily understood by those skilled in the art.

The term "light chain" when used in reference to an antibody refers to two distinct types, called kappa (κ) or lambda (λ) based on the amino acid sequence of the constant domains. Light chain amino acid sequences are well known in the art. In certain embodiments, the light chain is a human light chain.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only an epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al., *Nature* 1975, 256:495-497, or may be isolated from phage libraries using the techniques as described herein. Other methods for the preparation of clonal cell lines and of monoclonal antibodies expressed thereby are well known in the art. See, e.g., *Short Protocols in Molecular Biology*, Chapter 11 (Ausubel et al., eds., John Wiley and Sons, New York, 5th ed. 2002). Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same or to different epitopes within the protein. Methods for producing polyclonal antibodies are known in the art. See, e.g., *Short Protocols in Molecular Biology*, Chapter 11 (Ausubel et al., eds., John Wiley and Sons, New York, 5th ed. 2002).

The term "variable region" or "variable domain" refers to a portion of a light or heavy chain of an antibody, typically ranging from about 120 to about 130 amino acids at the amino terminal of the heavy chain and from about 100 to about 110 amino acids at the amino terminal of the light chain, which differs extensively in sequence among antibodies and confers the binding specificity of each antibody to its particular antigen. The variability in sequence is concentrated in those regions called complementarity determining regions (CDRs), while the more conserved regions in the variable domain are called framework regions (FR). The CDRs of the light and heavy chains are primarily responsible for the interaction of the antibody with antigen. Numbering of amino acid positions used herein is according to the Kabat numbering, as in Kabat et al., *Sequences of Proteins of Immunological Interest*, U.S. Department of Health and Human Services, NIH Publication No. 91-3242 (5th ed. 1991). In some embodiments, the variable region is a human variable region.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control mRNA level. Alternatively, an mRNA can be "downregulated", or expressed at a lower level, in response to administration of certain compounds or other agents. A downregulated mRNA can be, for example, present at a level of about 99%, about 95%, about 90%, about 80%, about 70%, about 60%, about 50%, about 40%, about 30%, about 20%, about 10%, about 1%, or less of the comparative control mRNA level.

Similarly, the level of a polypeptide or protein biomarker from a patient sample can be increased when treated with a drug, as compared to a non-treated control. This increase can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control protein level. Alternatively, the level of a protein biomarker can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control protein level.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition. An mRNA from a patient sample can be "upregulated" when treated with a drug, as compared to a non-treated control. This upregulation can be, for example, an increase of about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control mRNA level. Alternatively, an mRNA can be "downregulated", or expressed at a lower level, in response to administration of certain compounds or other agents. A downregulated mRNA can be, for example, present at a level of about 99%, about 95%, about 90%, about 80%, about 70%, about 60%, about 50%, about 40%, about 30%, about 20%, about 10%, about 1%, or less of the comparative control mRNA level.

Similarly, the level of a polypeptide or protein biomarker from a patient sample can be increased when treated with a drug, as compared to a non-treated control. This increase can be about 5%, about 10%, about 20%, about 30%, about 40%, about 50%, about 60%, about 70%, about 80%, about 90%, about 100%, about 200%, about 300%, about 500%, about 1,000%, about 5,000%, or more of the comparative control protein level. Alternatively, the level of a protein biomarker can be decreased in response to administration of certain compounds or other agents. This decrease can be, for example, present at a level of about 99%, about 95%, about 90%, about 80%, about 70%, about 60%, about 50%, about 40%, about 30%, about 20%, about 10%, about 1%, or less of the comparative control protein level.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

5.2 BIOMARKERS AND METHODS OF USE THEREOF

The methods provided herein are based, in part, on the finding that lenalidomide-responsive ATL cell lines have higher ratio of the mRNA expression level of CRBN to IKZF1 and CRBN to IKZF2 as compared with non-responsivie ATL cell lines and other cell lines. Thus, in one aspect, provided herein are methods for identifying a cancer patient (e.g., ATL patient) who is likely to be responsive to a treatment compound (e.g., lenalidomide), or predicting or monitoring the responsiveness of a cancer patient (e.g., ATL patient) to a treatment compound (e.g., lenalidomide), using the levels of two biomarkers and/or the ratio thereof.

In some embodiments, the level of each of the two biomarkers is determined, and the patient is determined to be likely to be responsive to a treatment compound is the level of one biomarker is higher than a reference level and the level of the other biomarker is lower than a reference level. In more specific embodiments, the ratio of the two biomarkers is determined, and the subject is determined to be likely to be responsive to a treatment compound if the ratio of the two biomarkers is different from a reference ratio.

Thus, in some embodiments, provided herein is a method of identifying a subject having a cancer who is likely to be responsive to a treatment compound, comprising:

(a) obtaining a sample from the subject;

(b) determining the ratio of a first biomarker level to a second biomarker level in the sample from the subject, wherein at least one of the biomarkers is a CRBN-associated protein; and (c) diagnosing the subject as being likely to be responsive to the treatment compound if the ratio of the biomarker levels in the sample of the subject is different from a reference ratio of the biomarker levels.

In another aspect, provided herein is a method of predicting the responsiveness of a subject having or suspected of having a cancer to a treatment compound, comprising:

(a) obtaining a sample from the subject;

(b) determining the ratio of a first biomarker level to a second biomarker level in the sample from the subject, wherein at least one of the biomarkers is a CRBN-associated protein;

(c) diagnosing the subject as being likely to be responsive to a treatment of the cancer with the treatment compound if the ratio of the biomarker levels in the sample is different from the ratio of the biomarker levels obtained from a reference sample.

In some embodiments, the methods provided herein further comprise administering a therapeutically effective amount of the treatment compound to the subject diagnosed to be likely to be responsive to the treatment compound.

In another aspect, provided herein is a method of treating a cancer, comprising:

(a) obtaining a sample from a subject having a cancer;

(b) determining the ratio of a first biomarker level to a second biomarker level in the sample from the subject, wherein at least one of the biomarkers is a CRBN-associated protein;

(c) diagnosing the subject as being likely to be responsive to a treatment compound if the ratio of the biomarker levels in the sample of the subject is different from a reference ratio of the biomarker levels; and (d) administering a therapeutically effective amount of the treatment compound to the subject diagnosed to be likely to be responsive to the treatment compound.

In some embodiments, in step (c) diagnosing the subject as being likely to be responsive to a treatment compound if the ratio of the biomarker levels in the sample of the subject is higher than a reference ratio of the biomarker levels. In other embodiments, in step (c) diagnosing the subject as being likely to be responsive to a treatment compound if the ratio of the biomarker levels in the sample of the subject is lower than a reference ratio of the biomarker levels.

In yet another aspect, provided herein is a method of monitoring the efficacy of a treatment of a cancer in a subject with a treatment compound, comprising:

(a) administering a treatment compound to a subject having a cancer;

(b) obtaining a sample from the subject;

(c) determining the ratio of a first biomarker level to a second biomarker level in the sample from the subject, wherein at least one of the biomarkers is a CRBN-associated protein; and (d) comparing the ratio of the biomarker levels in the sample with the ratio of the biomarker levels obtained from a reference sample, wherein a change in the ratio as compared to the reference is indicative of the efficacy of the treatment compound in treating the cancer in the subject.

In some embodiments of the methods provided herein, the administering a treatment compound to the sample from the subject having cancer is in vitro. In other embodiments, the administering a treatment compound to the sample from the subject having cancer is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In one embodiment, the cells are obtained from a cell line. In other embodiments, the cells are obtained from a subject having (or suspected of having) the cancer.

In some embodiments, an increased ratio as compared to the reference is indicative of the efficacy of the treatment compound in treating the cancer in the subject. In other embodiments, a decreased ratio as compared to the reference is indicative of the efficacy of the treatment compound in treating the cancer in the subject.

In some embodiments, the first biomarker is selected from the group comprising CRBN, IKZF1, and IKZF2. In some embodiments, the second biomarker is selected from the group comprising CRBN, IKZF1, and IKZF2. In some embodiments, the first biomarker and the second biomarker are selected from the group comprising CRBN, IKZF1, and IKZF2, and wherein the ratio of the biomarker levels changes as compared to a reference.

In some embodiments, the ratio of the biomarker levels increases as compared to a reference. In other embodiments, the ratio of the biomarker levels decreases as compared to a reference.

In some embodiments, the first biomarker is CRBN. In some embodiments, when the first biomarker is CRBN, the second biomarker is a substrate of CRBN. In other embodiments, when the first biomarker is CRBN, the second biomarker is not a substrate of CRBN.

In some embodiments, the first biomarker is CRBN and the second biomarker is IKZF1. In some embodiments, the ratio of the CRBN expression level to the IKZF1 expression level is higher than 2. In some embodiments, the ratio of the CRBN expression level to the IKZF1 expression level is higher than 3. In other embodiments, the ratio of the CRBN expression level to the IKZF1 expression level is higher than 4. In yet other embodiments, the ratio of the CRBN expression level to the IKZF1 expression level is higher than 5. In yet other embodiments, the ratio of the CRBN expression level to the IKZF1 expression level is higher than 6.

In other embodiments, the first biomarker is CRBN and the second biomarker is IKZF2. In some embodiments, the ratio of the CRBN expression level to the IKZF2 expression level is between 250 and 5000. In some embodiments, the ratio of the CRBN expression level to the IKZF2 expression level is between 500 and 5000. In other embodiments, the ratio of the CRBN expression level to the IKZF2 expression level is higher than 250. In other embodiments, the ratio of the CRBN expression level to the IKZF2 expression level is higher than 500. In other embodiments, the ratio of the CRBN expression level to the IKZF2 expression level is higher than 800. In other embodiments, the ratio of the CRBN expression level to the IKZF2 expression level is higher than 1000. In yet other embodiments, the ratio of the CRBN expression level to the IKZF2 expression level is higher than 1500. In yet other embodiments, the ratio of the CRBN expression level to the IKZF2 expression level is higher than 2000. In yet other embodiments, the ratio of the CRBN expression level to the IKZF2 expression level is higher than 2500.

The methods provided herein are also based, in part, on the finding that lenalidomide-responsive ATL cell lines have extremely low mRNA expression level of IKZF2. Thus, in another aspect, provided herein are methods for identifying a cancer patient (e.g., ATL patient) who is likely to be responsive to a treatment compound (e.g., lenalidomide), or predicting or monitoring the responsiveness of a cancer patient (e.g., ATL patient) to a treatment compound (e.g., lenalidomide), using the level of IKZF2.

In certain embodiments, provided herein is a method of identifying a subject having cancer who is likely to be responsive to a treatment compound, comprising:
 (a) obtaining a sample from a subject having cancer;
 (b) determining the level of a biomarker in the sample from the subject, wherein the biomarker is IKZF2; and
 (c) diagnosing the subject as being likely to be responsive to the treatment compound if the biomarker level in the sample of the subject is lower than a reference level of the biomarker.

In some embodiments, provided herein is a method of predicting the responsiveness of a subject having or suspected of having cancer to a treatment compound, comprising:
 (a) obtaining a sample from a subject having cancer;
 (b) determining the level of a biomarker in the sample from the subject, wherein the biomarker is IKZF2; and
 (c) diagnosing the subject as being likely to be responsive to the treatment compound in treating the cancer if the biomarker level in the sample of the subject is lower than a reference level of the biomarker.

In other embodiments, provided herein is a method of treating cancer, comprising:
 (a) obtaining a sample from a subject having cancer;
 (b) determining the level of a biomarker in the sample from the subject, wherein the biomarker is IKZF2;
 (c) diagnosing the subject as being likely to be responsive to a treatment compound if the biomarker level in the sample of the subject is lower than a reference level of the biomarker; and
 (d) administering a therapeutically effective amount of the treatment compound to the subject diagnosed as being likely to be responsive to the treatment compound.

In yet other embodiments, provided herein is method of monitoring the efficacy of a treatment compound in treating cancer in a subject, comprising:
 (a) administering a treatment compound to a subject having cancer;
 (b) obtaining a sample from the subject;
 (c) determining the level of a biomarker in the sample from the subject, wherein the biomarker is IKZF2; and
 (d) comparing the biomarker level in the sample with a reference level of the biomarker, wherein a lower biomarker level as compared to the reference is indicative of the efficacy of the treatment compound in treating the cancer in the subject.

In some embodiments of the methods provided herein, the administering a treatment compound to the sample from the subject having cancer is in vitro. In other embodiments, the administering a treatment compound to the sample from the subject having cancer is performed in vivo. In one embodiment, the cells are contacted with the compound for a period of time, e.g., 5, 10, 15, 20, 25, 30, 35, 40, 45, 50, or 55 minutes, or 1, 2, 3, 4, 5, 6, 7, 8, 9, 10, 11, 12, 13, 14, 15, 16, 17, 18, 19, 20, 21, 22, 23, or 24 hours, or 2 or 3 or more days. In one embodiment, the cells are obtained from a cell line. In other embodiments, the cells are obtained from a subject having (or suspected of having) the cancer.

In some embodiments, the treatment compound is determined to have efficacy in treating the cancer in the subject when the level of IKZF2 less than 50% of the reference level of IKZF2. In some embodiments, the treatment compound is determined to have efficacy in treating the cancer in the subject when the level of IKZF2 less than 40% of the reference level of IKZF2. In some embodiments, the treatment compound is determined to have efficacy in treating the cancer in the subject when the level of IKZF2 less than 30% of the reference level of IKZF2. In some embodiments, the treatment compound is determined to have efficacy in treating the cancer in the subject when the level of IKZF2 less than 20% of the reference level of IKZF2. In some embodiments, the treatment compound is determined to have efficacy in treating the cancer in the subject when the level of IKZF2 less than 10% of the reference level of IKZF2. In some embodiments, the treatment compound is determined to have efficacy in treating the cancer in the subject when the level of IKZF2 less than 5% of the reference level of IKZF2. In some embodiments, the treatment compound is determined to have efficacy in treating the cancer in the subject when the level of IKZF2 less than 1% of the reference level of IKZF2. In some embodiments, the treatment compound is determined to have efficacy in treating the cancer in the subject when the level of IKZF2 less than 0.5% of the reference level of IKZF2. In some embodiments, the treatment compound is determined to have efficacy in treating the cancer in the subject when the level of IKZF2 less than 0.1% of the reference level of IKZF2.

In some embodiments, the mRNA level of IKZF2 is used as a biomarker. In some embodiments, a relative biomarker mRNA level is in reference to the mRNA level of a housekeeping gene (e.g., GAPDH, β-actin, or the like). In some embodiment, the subject is determined as being likely to be responsive to a treatment compound if the relative mRNA level of IKZF2 is lower than 1 to 0.00001. In one embodiment, the relative IKZF2 mRNA level is lower than 1. In another embodiment, the relative IKZF2 mRNA level is lower than 0.5. In yet another embodiment, the relative IKZF2 mRNA level is lower than 0.1. In still another embodiment, the relative IKZF2 mRNA level is lower than 0.05. In another embodiment, the relative IKZF2 mRNA level is lower than 0.01. In one embodiment, the relative IKZF2 mRNA level is lower than 0.005. In another embodiment, the relative IKZF2 mRNA level is lower than 0.004. In yet another embodiment, the relative IKZF2 mRNA level is lower than 0.003. In still another embodiment, the relative IKZF2 mRNA level is lower than 0.002. In another embodiment, the relative IKZF2 mRNA level is lower than 0.001. In one embodiment, the relative IKZF2 mRNA level is lower than 0.0005.

In some embodiments of the various methods provided herein, the reference is prepared by using a control sample obtained from the subject having a cancer but not responsive to the compound treatment; and wherein the control sample is from the same source as the sample. In other embodiments, the reference is prepared by using a control sample obtained from a healthy subject not having the cancer; and wherein the control sample is from the same source as the sample.

In some embodiments of the various methods provided herein, the cancer is a leukemia. In some embodiments, the cancer is a lymphoma. In other embodiments, the cancer is an Adult T-cell Leukemia (ATL). In other embodiments, the cancer is relapsed, refractory or resistant to conventional therapy. In other embodiments, the cancer is a relapsed or refracted ATL.

In some embodiments of the various methods provided herein, the treatment compound is an immunomodulatory compound. In some embodiments, the treatment compound is lenalidomide.

In a specific embodiment of the various methods provided herein, the treatment compound is lenalidomide and the cancer is ATL.

In some embodiments, the level of the biomarker is measured by determining the protein level of the biomarker. In some embodiments, the methods provided herein comprise contacting proteins within the sample with a first antibody that immunospecifically binds to the biomarker protein. In some embodiments, the methods provided herein further comprise:

(i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody;

(ii) detecting the presence of the second antibody bound to the proteins; and (iii) determining the amount of the biomarker protein based on the amount of the detectable label in the second antibody.

In other embodiments, the methods provided herein further comprise:

(i) contacting the biomarker protein bound to the first antibody with a second antibody with a detectable label, wherein the second antibody immunospecifically binds to the first antibody;

(ii) detecting the presence of the second antibody bound to the proteins; and (iii) determining the amount of the biomarker protein based on the amount of the detectable label in the second antibody.

In other embodiments, the level of the biomarker is measured by determining the mRNA level of the biomarker. In yet other embodiments, the level of the biomarker is measured by determining the cDNA level of the biomarker. In some embodiments, the level of the biomarker is measured using quantitative PCR (qPCR). In some embodiments, the biomarker mRNA level is the relative mRNA level of the biomarker. In some embodiments, the relative biomarker mRNA level is in reference to the mRNA level of a housekeeping gene (e.g., GAPDH, belta-actin, or the like).

In some embodiments of the various methods provided herein, the patients include those who have been previously treated for cancer but are non-responsive to standard therapies, as well as those who have not previously been treated. The present disclosure also encompasses methods of treating patients regardless of patient's age, although some diseases or disorders are more common in certain age groups. The application further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In certain embodiments, a therapeutically or prophylactically effective amount of a treatment compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiment, a therapeutically or prophylactically effective amount is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg every other day.

In certain embodiments, the therapeutically or prophylactically effective amount is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of a treatment compound, or an enantiomer or a mixture of enantiomers thereof, or a pharmaceutically acceptable salt, solvate, hydrate, co-crystal, clathrate, or polymorph thereof, for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg per day.

In a specific embodiment, the recommended starting dosage may be 0.5, 1, 2, 3, 4, 5, 10, 15, 20, 25, or 50 mg per day. In another embodiment, the recommended starting dosage may be 0.5, 1, 2, 3, 4, or 5 mg per day. The dose may be escalated to 15, 20, 25, 30, 35, 40, 45, and 50 mg/day. In a specific embodiment, the compound can be administered in an amount of about 25 mg/day to patients with lymphoma, e.g., ATL. In a particular embodiment, the compound can be administered in an amount of about 10 mg/day to patients with lymphoma, including ATL.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, from about 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m2/day. One of ordinary skill in the art would readily know how to convert doses from mg/kg/day to mg/m2/day to given either the height or weight of a subject or both (see, www.fda.gov/ cder/cancer/animalframe.htm). For example, a dose of 1 mg/kg/day for a 65 kg human is approximately equal to 38 mg/m2/day.

In certain embodiments, the amount of a compound administered is sufficient to provide a plasma concentration of the compound at steady state, ranging from about 0.001 to about 500 µM, from about 0.002 to about 200 µM, from about 0.005 to about 100 µM, from about 0.01 to about 50 µM, from about 1 to about 50 µM, from about 0.02 to about 25 µM, from about 0.05 to about 20 µM, from about 0.1 to about 20 µM, from about 0.5 to about 20 µM, or from about 1 to about 20 µM.

In other embodiments, the amount of a compound administered is sufficient to provide a plasma concentration of the compound at steady state, ranging from about 5 to about 100 nM, from about 5 to about 50 nM, from about 10 to about 100 nM, from about 10 to about 50 nM, or from about 50 to about 100 nM.

As used herein, the term "plasma concentration at steady state" is the concentration reached after a period of administration of a compound provided herein, e.g., lenalidomide, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time-dependent curve of the plasma concentration of the compound.

In certain embodiments, the amount of a compound administered is sufficient to provide a maximum plasma concentration (peak concentration) of the compound, ranging from about 0.001 to about 500 µM, from about 0.002 to about 200 µM, from about 0.005 to about 100 µM, from about 0.01 to about 50 µM, from about 1 to about 50 µM, from about 0.02 to about 25 µM, from about 0.05 to about 20 µM, from about 0.1 to about 20 µM, from about 0.5 to about 20 µM, or from about 1 to about 20 µM.

In certain embodiments, the amount of a compound administered is sufficient to provide a minimum plasma concentration (trough concentration) of the compound, ranging from about 0.001 to about 500 µM, from about 0.002 to about 200 µM, from about 0.005 to about 100 µM, from about 0.01 to about 50 µM, from about 1 to about 50 µM, from about 0.01 to about 25 µM, from about 0.01 to about 20 µM, from about 0.02 to about 20 µM, from about 0.02 to about 20 µM, or from about 0.01 to about 20 µM.

In certain embodiments, the amount of a compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

Depending on the disease to be treated and the subject's condition, the compound provided herein, e.g., lenalidomide, or an enantiomer or a mixture of enantiomers thereof, or a pharmaceutically acceptable salt, solvate, hydrate, co-crystal, clathrate, or polymorph thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The compound provided herein, e.g., lenalidomide, or an enantiomer or a mixture of enantiomers thereof, or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants, and vehicles, appropriate for each route of administration.

In one embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered orally. In another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered parenterally. In yet another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered intravenously.

The compound provided herein, e.g., lenalidomide, or an enantiomer or a mixture of enantiomers thereof, or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Therasse et al., *J. Natl. Cancer Inst.* 2000, 92(3):205-216. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound provided herein, e.g., lenalidomide, or an enantiomer or a mixture of enantiomers thereof, or a pharmaceutically acceptable salt, solvate, hydrate, co-crystal, clathrate, or polymorph thereof, can be administered once daily (QD) or divided into multiple daily doses such as twice daily (BID), three times daily (TID), and four times daily (QID). In addition, the administration can be continuous (i.e., daily for consecutive days or every day) or intermittent, e.g., in cycles (i.e., including days, weeks, or months of rest without drug). As used herein, the term "daily" is intended to mean that a therapeutic compound, such as the compound provided herein, e.g., lenalidomide, is administered once or more than once each day, for example, for a period of time. The term "continuous" is intended to mean that a therapeutic compound, such as the compound provided herein, e.g., lenalidomide, is administered daily for an uninterrupted period of at least 10 days to 52 weeks. The term "intermittent" or "intermittently" as used herein is intended to mean stopping and starting at either regular or irregular intervals. For example, intermittent administration of the compound provided herein, e.g., lenalidomide, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound provided herein, e.g., lenalidomide, is administered daily or continuously but with a rest period. In certain embodiments, the rest period is the same length as the treatment period. In other embodiments, the rest period has different length from the treatment period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once a day. In another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered twice a day. In yet another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered three times a day. In still another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered four times a day.

In certain embodiments, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day for one week, two weeks, three weeks, or four weeks. In one embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day for one week. In another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day for two weeks. In yet another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day for three weeks. In still another embodiment, the compound provided herein, e.g., lenalidomide, or an enantiomer or a mixture of enantiomers thereof, or a pharmaceutically acceptable salt, solvate, hydrate, co-crystal, clathrate, or polymorph thereof, is administered once per day for four weeks.

In some embodiments of the various methods provided herein, the method further comprises administering a therapeutically effective amount of a second active agent or a support care therapy. The second active agents can be large molecules (e.g., proteins) or small molecules (e.g., synthetic inorganic, organometallic, or organic molecules). In some embodiments, the second active agent is a therapeutic antibody that specifically binds to a cancer antigen, hematopoietic growth factor, cytokine, anti-cancer agent, antibiotic, cox-2 inhibitor, immunomodulatory agent, immunosuppressive agent, corticosteroid, or a pharmacologically active mutant or derivative thereof.

In some embodiments, the second active agents are small molecules that can alleviate adverse effects associated with the administration of a compound provided herein, or an enantiomer or a mixture of enantiomers thereof, or a pharmaceutically acceptable salt, solvate, hydrate, co-crystal, clathrate, or polymorph thereof. Many small molecule second active agents are believed to be capable of providing a synergistic effect when administered with (e.g., before, after, or simultaneously) a compound provided herein, or an enantiomer or a mixture of enantiomers thereof, or a pharmaceutically acceptable salt, solvate, hydrate, co-crystal, clathrate, or polymorph thereof. Examples of small molecule second active agents include, but are not limited to, anti-cancer agents, antibiotics, immunosuppressive agents, and steroids.

5.3 METHODS OF DETECTING AND QUANTIFYING BIOMARKERS

In certain embodiments, provided herein is a method of detecting and/or quantifying biomarkers, comprising:
 (a) obtaining a sample from the subject
 (b) determining the ratio of a first biomarker level to a second biomarker level in the sample from the subject, wherein at least one of the biomarkers is a CRBN-associated protein; and
 (c) comparing the ratio of the biomarker levels in the sample of the subject with a reference ratio of the biomarker levels.

In certain embodiments, provided herein is a method of detecting and/or quantifying biomarkers, comprising:
 (a) administering a treatment compound to a subject having a cancer;
 (b) obtaining a sample from the subject;
 (c) determining the ratio of a first biomarker level to a second biomarker level in the sample from the subject, wherein at least one of the biomarkers is a CRBN-associated protein; and
 (d) comparing the ratio of the biomarker levels in the sample with the ratio of the biomarker levels obtained from a reference sample.

In some embodiments, the reference is prepared by using a control sample obtained from the subject having a cancer but not responsive to the compound treatment; and wherein the control sample is from the same source as the sample. In other embodiments, the reference is prepared by using a control sample obtained from a healthy subject not having the cancer; and wherein the control sample is from the same source as the sample.

In some embodiments, the cancer is a leukemia. In some embodiments, the cancer is a lymphoma. In other embodiments, the cancer is an Adult T-cell Leukemia (ATL). In other embodiments, the cancer is relapsed, refractory or resistant to conventional therapy. In other embodiments, the cancer is a relapsed or refracted ATL.

In some embodiments, the treatment compound is an immunomodulatory compound. In some embodiments, the treatment compound is lenalidomide.

In a specific embodiment, the treatment compound is lenalidomide and the cancer is ATL.

In some embodiments, the first biomarker is selected from the group comprising CRBN, IKZF1, and IKZF2. In some embodiments, the second biomarker is selected from the group comprising CRBN, IKZF1, and IKZF2. In some embodiments, the first biomarker and the second biomarker are selected from the group comprising CRBN, IKZF1, and IKZF2, and wherein the ratio of the biomarker levels changes as compared to a reference.

In some embodiments, the ratio of the biomarker levels increases as compared to a reference. In other embodiments, the ratio of the biomarker levels decreases as compared to a reference.

In some embodiments, the first biomarker is CRBN. In some embodiments, when the first biomarker is CRBN, the second biomarker is a substrate of CRBN. In other embodiments, when the first biomarker is CRBN, the second biomarker is not a substrate of CRBN.

In some embodiments, the first biomarker is CRBN and the second biomarker is IKZF1. In some embodiments, the ratio of the CRBN expression level to the IKZF1 expression level is higher than 3. In other embodiments, the ratio of the CRBN expression level to the IKZF1 expression level is higher than 4. In yet other embodiments, the ratio of the CRBN expression level to the IKZF1 expression level is higher than 5.

In other embodiments, the first biomarker is CRBN and the second biomarker is IKZF2. In some embodiments, the ratio of the CRBN expression level to the IKZF2 expression level is between 500 and 5000. In other embodiments, the ratio of the CRBN expression level to the IKZF2 expression level is higher than 500. In other embodiments, the ratio of the CRBN expression level to the IKZF2 expression level is higher than 1000. In yet other embodiments, the ratio of the CRBN expression level to the IKZF2 expression level is higher than 1500. In yet other embodiments, the ratio of the CRBN expression level to the IKZF2 expression level is higher than 2500.

In some embodiments, the level of the biomarker is measured by determining the protein level of the biomarker. In other embodiments, the level of the biomarker is measured by determining the mRNA level of the biomarker. In yet other embodiments, the level of the biomarker is measured by determining the cDNA level of the biomarker. In some embodiments, the level of the biomarker is measured using quantative PCR (qPCR).

In certain embodiments, provided herein are methods of detecting and quantifying the protein level of a biomarker provided herein from a biological sample, contacting proteins within the sample with a first antibody that immunospecifically binds to the biomarker protein. In some embodiments, the methods provided herein further comprise (i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody; (ii) detecting the presence of second antibody bound to the proteins; and (iii) determining the amount of the biomarker protein based on the amount of detectable label in the second antibody. In other embodiments, the methods provided herein further comprise (i) contacting the biomarker protein bound to the first antibody with a second antibody with a detectable label, wherein the second antibody immunospecifically binds to the first antibody; (ii) detecting the presence of second antibody bound to the proteins; and (iii) determining the amount of the biomarker protein based on the amount of detectable label in the second antibody.

In some embodiments of the various methods provided herein, the method comprises using dual staining immunohistochemistry to determine the level of one or more biomarkers. In a dual staining immunohistochemistry assay, a first biomarker provided herein and a second biomarker are simultaneously detected using a first labeled antibody targeting a first biomarker provided herein and a second labeled antibody targeting a second biomarker. In some embodiments, the first biomarker is CRBN, and the second biomarker is IKZF1. In other embodiments, the first biomarker is CRBN, and the second biomarker is IKZF2.

Thus, in some embodiments, the method provided herein comprises (i) contacting proteins within a sample with a first antibody that immunospecifically binds to a first biomarker provided herein, the first antibody being coupled with a first detectable label; (ii) contacting the proteins within the sample with a second antibody that immunospecifically binds to a second biomarker, the second antibody being coupled with a second detectable label; (iii) detecting the presence of the first antibody and the second antibody bound to the proteins; and (iv) determining the levels of the two biomarkers provided herein based on the amount of detectable label in the first antibody and the second antibody, and determining the ratio of the levels of the two biomarkers.

In certain embodiments, provided herein are methods of detecting and quantifying the RNA (e.g., mRNA) level of a biomarker provided herein from a biological sample, comprising: (a) obtaining RNA from a sample; (b) contacting the RNA with a primer comprising a sequence specifically binding to a sequence in the RNA to generate a first DNA molecule having a sequence complementary to said RNA; (c) amplifying the DNA corresponding to a segment of a gene encoding the biomarker; and (d) determining the RNA level of the biomarker based on the amount of the amplified DNA.

In certain embodiments of the various methods provided herein, the two or more of the steps are performed sequentially. In other embodiments of the methods provided herein, two or more of steps are performed in parallel (e.g., at the same time).

Exemplary assays provided herein for the methods of detecting and quantifying the protein level of a biomarker, are immunoassays, such as Western blot analysis and enzyme-linked immunosorbent assay (ELISA) (e.g., a sandwich ELISA). An exemplary assay provided herein for the methods of detecting and quantifying the RNA level of a biomarker provided herein, or a combination thereof, is reverse transcription polymerase chain reaction (RT-PCR), e.g., quantitative PCR or qPCR.

In some embodiments, a statistical analysis or other analysis is performed on data from the assay utilized to measure an RNA transcript or protein. In certain specific embodiments, p value of those RNA transcripts or proteins differentially expressed is 0.1, 0.5, 0.4, 0.3, 0.2, 0.01, 0.05, 0.001, 0.005, or 0.0001. In specific embodiments, a false discovery rate (FDR) of 10%, 9%, 8%, 7%, 6%, 5%, 4%, 3%, 2%, 1% or less is selected.

5.3.1 Methods of Detecting mRNA Levels in a Sample

Several methods of detecting or quantitating mRNA levels are known in the art and are suitable for use in the methods provided herein for measuring the level of the biomarker. Exemplary methods include, but are not limited to, Northern blots, ribonuclease protection assays, and PCR-based methods. When the biomarker is an mRNA molecule, the mRNA sequence, or a fragment thereof, can be used to prepare a probe that is at least partially complementary. The probe can then be used to detect the mRNA sequence in a sample, using any suitable assay, such as PCR-based methods, Northern blotting, or a dipstick assay.

In other embodiments, a nucleic acid assay for testing for immunomodulatory activity in a biological sample can be prepared. An assay typically contains a solid support and at least one nucleic acid contacting the support, where the nucleic acid corresponds to at least a portion of an mRNA that has altered expression during an immunomodulatory treatment in a patient, such as the mRNA of a biomarker (e.g., CRBN, IKZF1, or IKZF2). The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In some embodiments, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2',4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258) phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

In some embodiments, the mRNA sequences comprise at least one mRNA of a biomarker provided herein. In some embodiments, the biomarker is selected from the group consisting of mRNA of CRBN, IKZF1, IKZF2, or a fragment thereof. In one embodiment, the mRNA is CRBN mRNA. In another embodiment, the mRNA is IKZF1 mRNA. In yet another embodiment, the mRNA is IKZF2 mRNA.

In certain embodiments, the mRNA levels of more than one biomarkers provided herein are measured. In some embodiments, the ratio of the mRNA levels of two different biomarkers provided herein is calculated. In one embodiment, the ratio is the CRBN mRNA level to the IKZF1 mRNA level. In another embodiment, the ratio is the CRBN mRNA level to the IKZF2 mRNA level.

The nucleic acids may be present in specific, addressable locations on a solid support, each corresponding to at least a portion of mRNA sequences that are differentially expressed upon treatment of an immunomodulatory compound in a cell or a patient.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 1992, 258:818-821 and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 1981, 21:470-480; Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect the expression of CRBN or a protein that is directly or indirectly affected by CRBN. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., *Clin. Sci.* 2005, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TaqMan® Sequence Detection Chemistry. For example, TaqMan® Gene Expression Assays can be used, following the manufacturer's instructions. These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the $C_T$), the data can be analyzed, for example, using a 7500 Real-Time PCR System Sequence Detection software v1.3 using the comparative $C_T$ relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

Techniques known to one skilled in the art may be used to measure the amount of an RNA transcript(s). In some embodiments, the amount of one, two, three, four, five or more RNA transcripts is measured using deep sequencing, such as ILLUMINA® RNASeq, ILLUMINA® next generation sequencing (NGS), ION TORRENT™ RNA next generation sequencing, 454™ pyrosequencing, or Sequencing by Oligo Ligation Detection (SOLID™). In other embodiments, the amount of multiple RNA transcripts is measured using a microarray and/or gene chip. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art.

5.3.2 Methods of Detecting Polypeptide or Protein Biomarkers

When the biomarker is a protein, polypeptide, or peptide, several protein detection and quantitation methods can be used to measure the level of the biomarker. Any suitable protein quantitation method can be used in the methods provided herein. In certain embodiments, antibody-based methods are used. Exemplary methods that can be used include, but are not limited to, immunoblotting (Western blot), enzyme-linked immunosorbent assay (ELISA), immunohistochemistry, flow cytometry, cytometric bead array, and mass spectroscopy. In certain embodiments, a biomarker protein is detected using mass spectroscopy. Several types of ELISA are commonly used, including direct ELISA, indirect ELISA, and sandwich ELISA.

In some embodiments, the polypeptide or protein comprises at least one polypeptide or protein of a biomarker provided herein. In some embodiments, the biomarker is selected from the group consisting of polypeptide or protein of CRBN, IKZF1, IKZF2, or a fragment thereof. In one embodiment, the polypeptide or protein is CRBN polypeptide or protein. In another embodiment, the polypeptide or protein is IKZF1 polypeptide or protein. In yet another embodiment, the polypeptide or protein is IKZF2 polypeptide or protein.

In certain embodiments, the polypeptide or protein levels of more than one biomarkers provided herein are measured. In some embodiments, the ratio of the polypeptide or protein levels of two different biomarkers provided herein is calculated. In one embodiment, the ratio is the CRBN polypeptide or protein level to the IKZF1 polypeptide or protein level. In another embodiment, the ratio is the CRBN polypeptide or protein level to the IKZF2 polypeptide or protein level.

5.4 SUBJECTS AND SAMPLES

In certain embodiments, the various methods provided herein use samples (e.g., biological samples) from subjects or individuals (e.g., patients). The subject can be a patient, such as, a patient with cancer (e.g., ATL). The subject can be a mammal, for example, a human. The subject can be male or female, and can be an adult, child, or infant. Samples can be analyzed at a time during an active phase of cancer (e.g., ATL), or when the cancer (e.g., ATL) is inactive. In certain embodiments, more than one sample from a subject can be obtained.

In certain embodiments, the sample used in the methods provided herein comprises body fluids from a subject. Non-limiting examples of body fluids include blood (e.g., whole blood), blood plasma, amniotic fluid, aqueous humor, bile, cerumen, cowper's fluid, pre-ej aculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., PCR Protocols (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., a compound provided in Section 5.6 below) to the subject.

5.5 TYPES OF CELLS

In certain embodiments, the sample used in the methods provided herein comprises a plurality of cells, such as cancer (e.g., ATL) cells. Such cells can include any type of cells, e.g., stem cells, blood cells (e.g., peripheral blood mononuclear cells), lymphocytes, B cells, T cells, monocytes, granulocytes, immune cells, or cancer cells.

As shown in Table 1, in certain embodiments, the cells in the methods provided herein can be obtained from a cell line. In some embodiments, the cells in the methods provided herein are ATL-patient derived cell lines. In other embodiments, the cells in the methods provided herein are HTLV-1 transformed cell lines. In yet other embodiments, the cells in the methods provided herein are HTLV-1 negative T-cell or malignant cell lines. In still other embodiments, the cells in the methods provided herein are non-ATL cancer derived cell lines (e.g., multiple myeloma cell lines). In certain embodiments, the ATL-patient derived cell line is selected from the group consisting of Hut102, ED40515, Su9T1, OATL4, OATL9, S1T, ST1, KOB, KK1, and SO4 cell lines. In other embodiments, the HTLV-1 transformed cell line is selected from the group consisting of MT-2, MT-4, and C8166 cell lines. In yet other embodiments, the HTLV-1 negative T-cell or malignant cell line is selected from the group consisting of HuT78, MOLT4, Jurkat, K562, and HL60 cell lines. In still other embodiments, non-ATL cancer derived cell line (e.g., multiple myeloma cell line) is selected from the group consisting of lenalidomide-responsive cell lines (e.g., NCI-H929) and lenalidomide-irresponsive cell lines (e.g., RPML-8226).

In one specific embodiment, the cell line is Hut102 cell line. In another embodiment, the cell line is ED40515 cell line. In yet another embodiment, the cell line is Su9T1 cell line. In still another embodiment, the cell line is OATL4 cell line. In certain embodiments, the cell line is OATL9 cell line. In some embodiments, the cell line is S1T cell line. In other embodiments, the cell line is ST1 cell line. In yet other embodiments, the cell line is KOB cell line. In still other embodiments, the cell line is KK1 cell line. In certain embodiments, the cell line is SO4 cell line. In one specific embodiment, the cell line is MT-2 cell line. In another embodiment, the cell line is MT-4 cell line. In yet another embodiment, the cell line is C8166 cell line. In still another embodiment, the cell line is HuT78 cell line. In certain embodiments, the cell line is MOLT4 cell line. In some embodiments, the cell line is Jurkat cell line. In other embodiments, the cell line is K562 cell line. In yet other embodiments, the cell line is HL60 cell line. In still other embodiments, the cell line is NCI-H929 cell line. In certain embodiments, the cell line is RPMI-8226 cell line.

In certain embodiments, the sample used in the methods provided herein is from a disease tissue, e.g., from an individual having cancer (e.g., ATL). In certain embodiments, the methods provided herein are useful for detecting gene rearrangement in cells from a healthy individual. In certain embodiments, the number of cells used in the methods provided herein can range from a single cell to about $10^9$ cells. In some embodiments, the number of cells used in the methods provided herein is about $1\times10^4$, about $5\times10^4$, about $1\times10^5$, about $5\times10^5$, about $1\times10^6$, about $5\times10^6$, about $1\times10^7$, about $5\times10^7$, about $1\times10^8$, about $5\times10^8$, or about $1\times10^9$.

The number and type of cells collected from a subject can be monitored, for example, by measuring changes in cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), by examining the morphology of cells using light or confocal microscopy, and/or by measuring changes in gene expression using techniques well known in the art, such as PCR and gene expression profiling. These techniques can be used, too, to identify cells that are positive for one or more particular markers.

In certain embodiments, subsets of cells are used in the methods provided herein. Methods of sorting and isolating specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc. Fluorescence activated cell sorting (FACS) is a well-known method for separating particles, including cells, based on the fluorescent properties of the particles (Kamarch, *Methods Enzymol*. 1987, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one embodiment, RNA (e.g., mRNA) or protein is purified from a tumor, and the presence or absence of a biomarker is measured by gene or protein expression analysis. In certain embodiments, the presence or absence of a biomarker is measured by quantitative real-time PCR (qRT-PCR), microarray, flow cytometry, or immunofluorescence. In other embodiments, the presence or absence of a biomarker is measured by ELISA or other similar methods known in the art.

5.6 COMPOUNDS

In some embodiments, the treatment compound (or compound) is an immunomodulatory compound.

As used herein and unless otherwise indicated, the term "immunomodulatory compound" encompasses certain small organic molecules that inhibit LPS induced monocyte production of TNF-α, IL-1β, IL-12, IL-6, MIP-1α, MCP-1, GM-CSF, G-CSF, and COX-2. Specific immunomodulatory compounds are provided herein.

TNF-α is an inflammatory cytokine produced by macrophages and monocytes during acute inflammation. TNF-α is responsible for a diverse range of signaling events within cells. Without being limited by a particular theory, one of the biological effects exerted by the immunomodulatory compounds provided herein is the reduction of myeloid cell TNF-α production. In certain embodiments, the immunomodulatory compounds provided herein enhance the degradation of TNF-α mRNA.

Examples of the immunomodulatory compounds provided herein include, but are not limited to, cyano and carboxy derivatives of substituted styrenes, such as those disclosed in U.S. Pat. No. 5,929,117; 1-oxo-2-(2,6-dioxo-3-fluoropiperidin-3-yl)-isoindolines and 1,3-dioxo-2-(2,6-dioxo-3-fluoropiperidine-3-yl)-isoindolines, such as those described in U.S. Pat. Nos. 5,874,448 and 5,955,476; tetra substituted 2-(2,6-dioxopiperdin-3-yl)-1-oxoisoindolines, such as those described in U.S. Pat. No. 5,798,368; 1-oxo- and 1,3-dioxo-2-(2,6-dioxopiperidin-3-yl)-isoindolines (e.g., 4-methyl derivatives of thalidomide), substituted 2-(2, 6-dioxopiperidin-3-yl) phthalimides, and substituted 2-(2,6-dioxopiperidin-3-yl)-1-oxoisoindoles, including but not limited to those disclosed in U.S. Pat. Nos. 5,635,517, 6,281, 230, 6,316,471, 6,403,613, 6,476,052, and 6,555,554; 1-oxo- and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindole-imide compounds, such as those described in U.S. Patent Application Publication Nos. 2003/0045552 and 2003/0096841, and International Patent Application Publication No. WO 02/059106. The disclosure of each of the patents and patent application publications identified herein is incorporated herein by reference in its entirety.

Various immunomodulatory compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular immunomodulatory compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33:2725-2736; Eliel, *Stereochemistry of Carbon Compounds* (McGraw-Hill, N Y, 1962); Wilen, *Tables of Resolving Agents and Optical Resolutions*, p. 268 (Eliel, ed., Univ. of Notre Dame Press, Notre Dame, Ind., 1972).

In certain embodiments, the immunomodulatory compound is 1-oxo- or 1,3-dioxo-2-(2,6-dioxopiperidin-3-yl)-isoindoline substituted with amino in the benzo ring, including those described in U.S. Pat. No. 5,635,517, the disclosure of which is incorporated herein by reference in its entirety.

In certain embodiments, the immunomodulatory compound has the structure of Formula I:

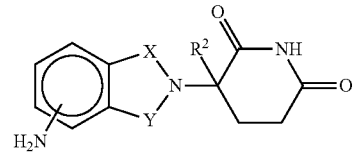

wherein one of X and Y is C=O the other of X and Y is C=O or CH$_2$, and R$^2$ is hydrogen or lower alkyl, in one embodiment, methyl.

In certain embodiments, the immunomodulatory compound is:

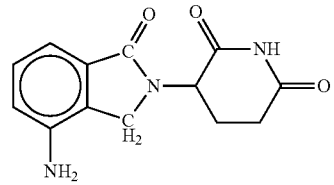

1-oxo-2-(2,6-dioxopiperidin-3-yl)-4-aminoisoindoline (lenalidomide);

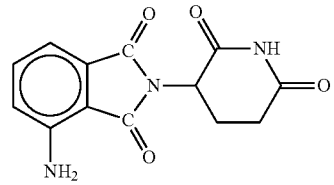

1,3-dioxo-2-(2,6-dioxopiperidin-3-yl)-4-aminoisoindoline (pomalidomide); or

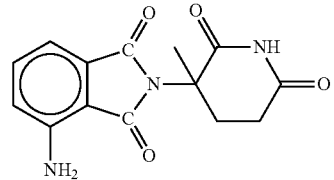

1,3-dioxo-2-(3-methyl-2,6-dioxopiperidin-3-yl)-4-aminoisoindole, or an optically pure isomer thereof. The immunomodulatory compounds can be obtained via standard synthetic methods. See U.S. Pat. No. 5,635,517, the disclosure of which is incorporated herein by reference in its entirety. The immunomodulatory compounds are also available from Celgene Corporation, Warren, N.J.

In certain embodiments, the immunomodulatory compound is lenalidomide. In certain embodiments, the immunomodulatory compound is pomalidomide.

In certain embodiments, the immunomodulatory compound is substituted 2-(2,6-dioxopiperidin-3-yl)-phthalimide or substituted 2-(2,6-dioxopiperidin-3-yl)-1-oxoisoindole, including those described in U.S. Pat. Nos. 6,281,230; 6,316,471; 6,335,349; 6,476,052; and International Application Publication No. WO 98/03502, the disclosure of each of which is incorporated herein by reference in its entirety.

In certain embodiments, the immunomodulatory compound is of formula:

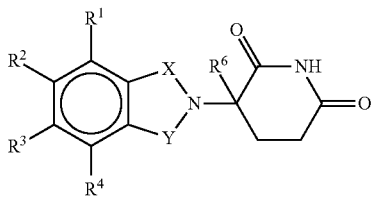

wherein:
one of X and Y is C=O and the other of X and Y is C=O or CH$_2$;
(i) each of R$^1$, R$^2$, R$^3$, and R$^4$, independently of the others, is halo, C$_{1-4}$ alkyl, or C$_{1-4}$ alkoxy; or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or C$_{1-8}$ alkyl;
R$^6$ is hydrogen, C$_{1-8}$ alkyl, benzyl, or halo;
provided that R$^6$ is other than hydrogen if X and Y are C=O and (i) each of R$^1$, R$^2$, R$^3$, and R$^4$ is fluoro or (ii) one of R$^1$, R$^2$, R$^3$, or R$^4$ is amino.

In certain embodiments, the immunomodulatory compound is of formula

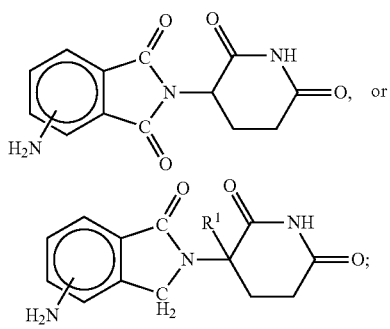

wherein R$^1$ is hydrogen or methyl.

In certain embodiments, the immunomodulatory compound used in the methods provided herein is enantiomerically pure (e.g. optically pure (R)- or (S)-enantiomer).

In another embodiment, the treatment compound is thalidomide, i.e., 2-(2,6-dioxopiperidin-3-yl)-1H-isoindole-1,3(2H)-dione.

In other embodiments, the treatment compound is 5-substituted quinazolinone, including those described in U.S. Pat. No. 7,635,700, the disclosure of which is incorporated herein by reference in its entirety.

In certain embodiments, the treatment compound is a compound having the structure of Formula IV:

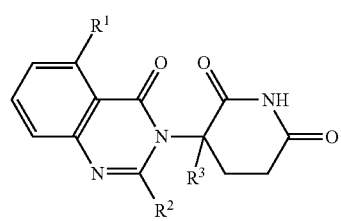

or a pharmaceutically acceptable salt, solvate, or stereoisomer thereof, wherein:

R$^1$ is:
hydrogen;
halo;
—(CH$_2$)$_n$OH;
C$_{1-6}$ alkyl, optionally substituted with one or more halo;
C$_{1-6}$ alkoxy, optionally substituted with one or more halo; or
—(CH$_2$)$_n$NHR$^a$, wherein R$^a$ is:
hydrogen;
C$_{1-6}$ alkyl, optionally substituted with one or more halo;
—(CH$_2$)$_n$-(6 to 10 membered aryl);
—C(O)—(CH$_2$)$_n$-(6 to 10 membered aryl) or —C(O)—(CH$_2$)$_n$-(5 to 10 membered heteroaryl), wherein the aryl or heteroaryl is optionally substituted with one or more of: halo; —SCF$_3$; C$_{1-6}$ alkyl, itself optionally substituted with one or more halo; or C$_{1-6}$ alkoxy, itself optionally substituted with one or more halo;
—C(O)—C$_{1-8}$ alkyl, wherein the alkyl is optionally substituted with one or more halo;
—C(O)—(CH$_2$)$_n$(C$_3$-C$_{10}$-cycloalkyl);
—C(O)—(CH$_2$)$_n$—NR$^b$R$^c$, wherein R$^b$ and R$^c$ are each independently:
hydrogen;
C$_{1-6}$ alkyl, optionally substituted with one or more halo;
C$_{1-6}$ alkoxy, optionally substituted with one or more halo; or
6 to 10 membered aryl, optionally substituted with one or more of: halo; C$_{1-6}$ alkyl, itself optionally substituted with one or more halo; or C$_{1-6}$ alkoxy, itself optionally substituted with one or more halo;
—C(O)—(CH$_2$)$_n$—O—C$_{1-6}$ alkyl; or
—C(O)—(CH$_2$)$_n$—O—(CH$_2$)$_n$-(6 to 10 membered aryl);
R$^2$ is: hydrogen; —(CH$_2$)$_n$OH; phenyl; —O—C$_{1-6}$ alkyl; or C$_{1-6}$ alkyl, optionally substituted with one or more halo;
R$^3$ is: hydrogen; or C$_{1-6}$ alkyl, optionally substituted with one or more halo; and
n is 0, 1, or 2.

In certain embodiments, the treatment compound is a compound having the structure of Formula V:

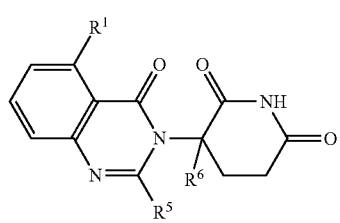

or a pharmaceutically acceptable salt, solvate, or stereoisomer thereof, wherein:
R$^4$ is: hydrogen; halo; —(CH$_2$)$_n$ OH; C$_{1-6}$ alkyl, optionally substituted with one or more halo; or C$_{1-6}$ alkoxy, optionally substituted with one or more halo
R$^5$ is: hydrogen; —(CH$_2$)$_n$OH; phenyl; —O—C$_{1-6}$ alkyl; or C$_{1-6}$ alkyl, optionally substituted with one or more halo;
R$^6$ is: hydrogen; or C$_{1-6}$ alkyl, optionally substituted with one or more halo; and
n is 0, 1, or 2.

In certain embodiments, the treatment compound is:
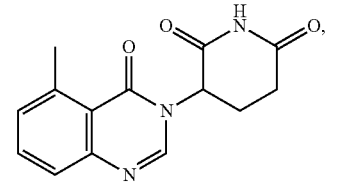
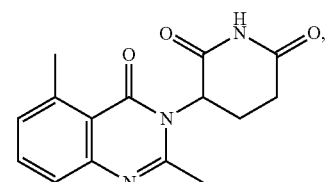
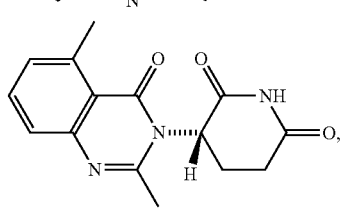
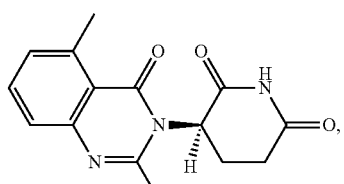
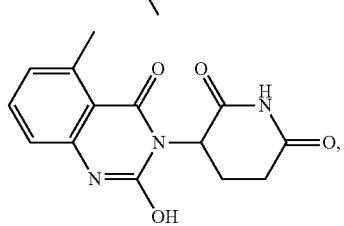
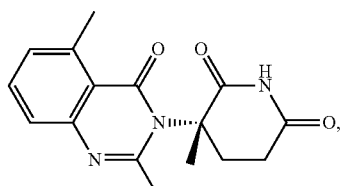
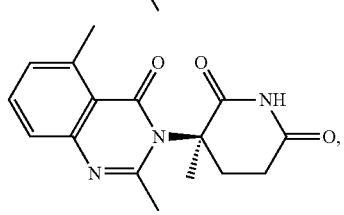
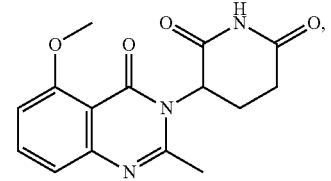
-continued
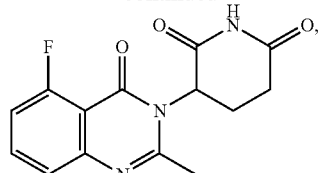
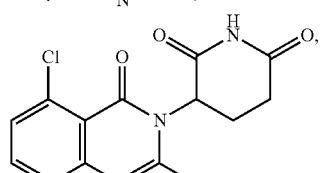
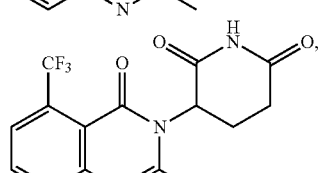
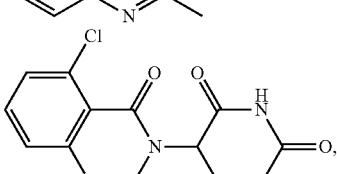
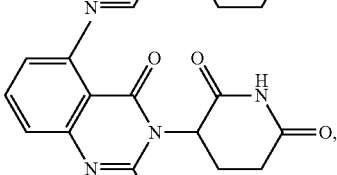
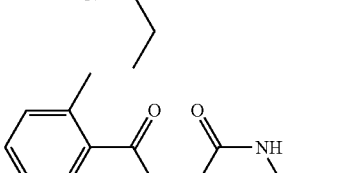
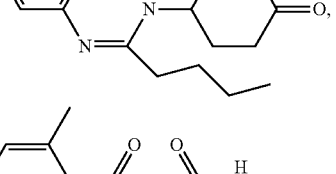
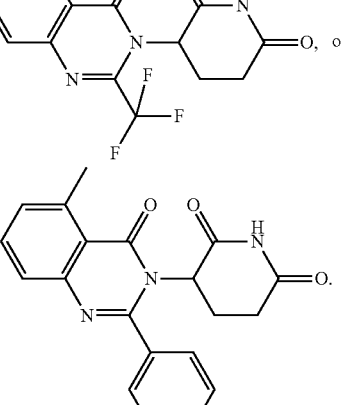
In certain embodiments, the treatment compound is a compound of Formula VI:

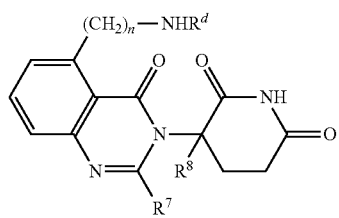

(VI)

or a pharmaceutically acceptable salt, solvate, or stereoisomer thereof, wherein:

$R^d$ is: hydrogen;
- $C_{1-6}$ alkyl, optionally substituted with one or more halo;
- —C(O)—$C_{1-8}$ alkyl, wherein the alkyl is optionally substituted with one or more halo;
- —C(O)—$(CH_2)_n$—$C_{3-10}$ cycloalkyl;
- —C(O)—$(CH_2)_n$—$NR^eR^f$, wherein $R^e$ and $R^f$ are each independently:
  - hydrogen;
  - $C_{1-6}$ alkyl, optionally substituted with one or more halo; or
  - $C_{1-6}$ alkoxy, optionally substituted with one or more halo; or
- —C(O)—$(CH_2)_n$—O—$C_{1-6}$ alkyl.

$R^7$ is: hydrogen; —$(CH_2)_nOH$; phenyl; —O—$C_{1-6}$ alkyl; or $C_{1-6}$ alkyl, optionally substituted with one or more halo;

$R^8$ is: hydrogen; or $C_{1-6}$ alkyl, optionally substituted with one or more halo; and n is 0, 1, or 2.

In certain embodiments, the treatment compound is:

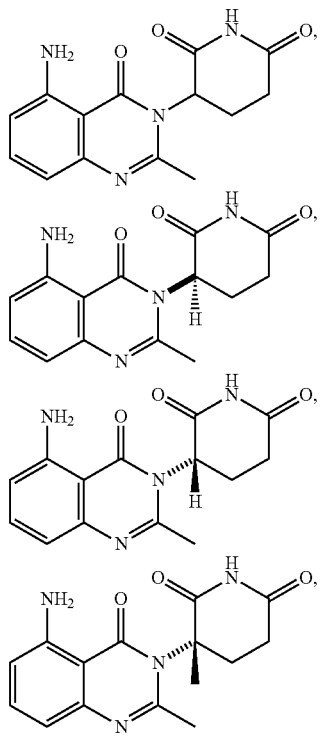

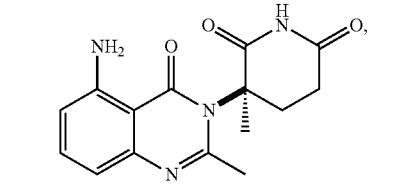

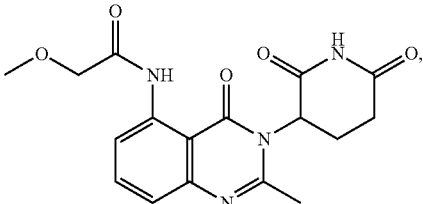

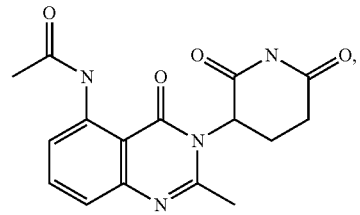

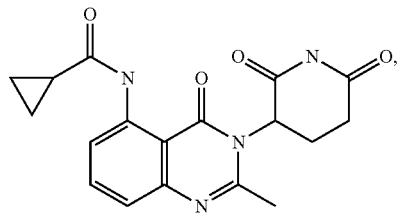

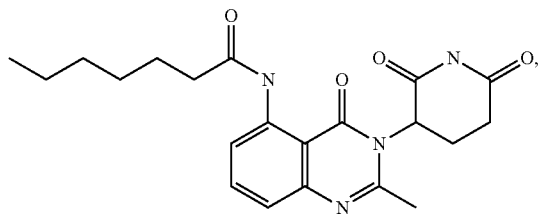

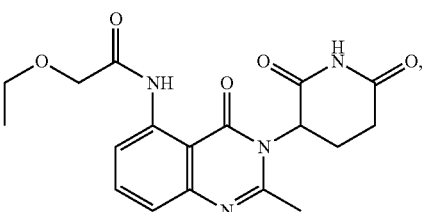

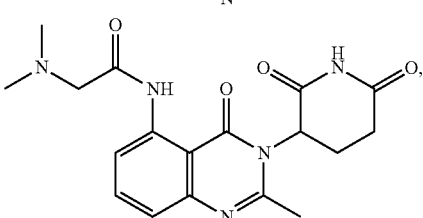

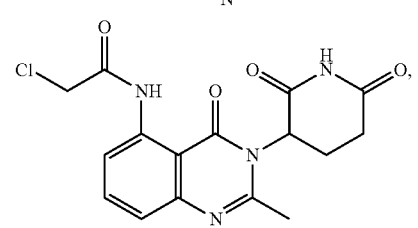

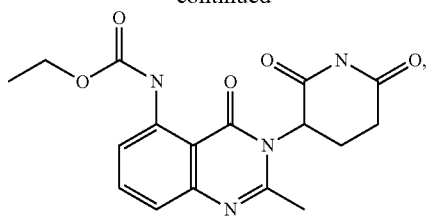

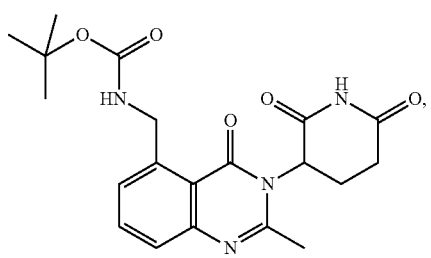

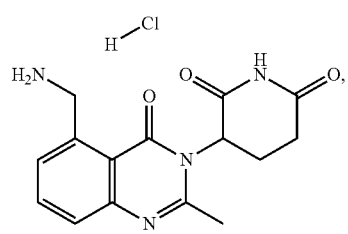

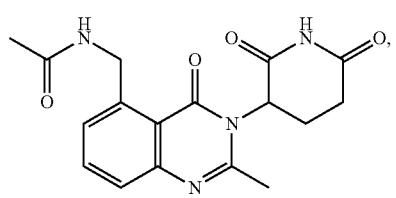

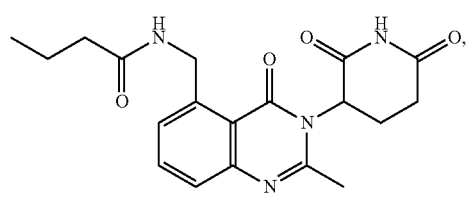

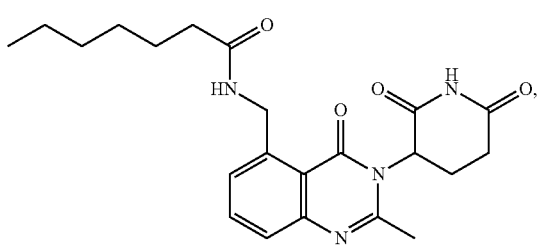

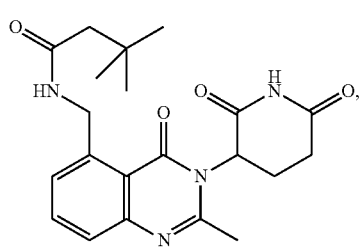

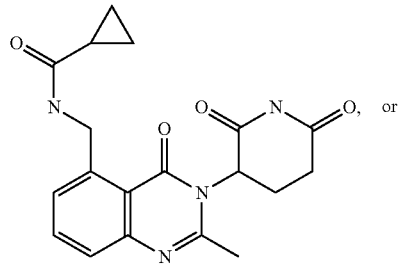

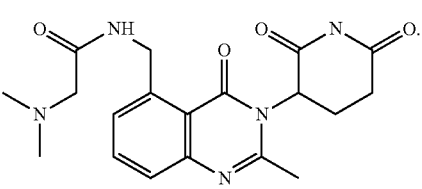

In certain embodiments, the treatment compound is 3-(5-amino-2-methyl-4-oxo-4H-quinazolin-3-yl)-piperidine-2,6-dione, or a stereoisomer thereof, or a pharmaceutically acceptable salt, solvate, hydrate, co-crystal, clathrate, or a polymorph thereof.

In certain embodiments, the treatment compound is a compound of Formula VII:

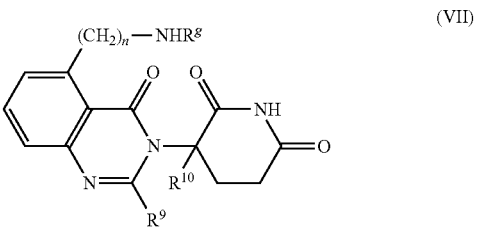

(VII)

or a pharmaceutically acceptable salt, solvate, or stereoisomers thereof, wherein:

$R^g$ is: —$(CH_2)_n$-(6 to 10 membered aryl);

—C(O)—$(CH_2)_n$-(6 to 10 membered aryl) or —C(O)—$(CH_2)_n$-(5 to 10 membered heteroaryl), wherein the aryl or heteroaryl is optionally substituted with one or more of: halo; —$SCF_3$; ($C_1$-$C_6$) alkyl, itself optionally substituted with one or more halo; or $C_{1-6}$ alkoxy, itself optionally substituted with one or more halo;

—C(O)—$(CH_2)_n$—$NHR^h$, wherein $R^h$ is: 6 to 10 membered aryl, optionally substituted with one or more of: halo; $C_{1-6}$ alkyl, itself optionally substituted with one or more halo; or $C_{1-6}$ alkoxy, itself optionally substituted with one or more halo; or —C(O)—$(CH_2)_n$—O—$(CH_2)_n$-(6 to 10 membered aryl);

$R^9$ is: hydrogen; —$(CH_2)_n$OH; phenyl; —O—$C_{1-6}$ alkyl; or $C_{1-6}$ alkyl, optionally substituted with one or more halo;

$R^{10}$ is: hydrogen; or $C_{1-6}$ alkyl, optionally substituted with one or more halo; and n is 0, 1, or 2.

In certain embodiments, the treatment compound is:
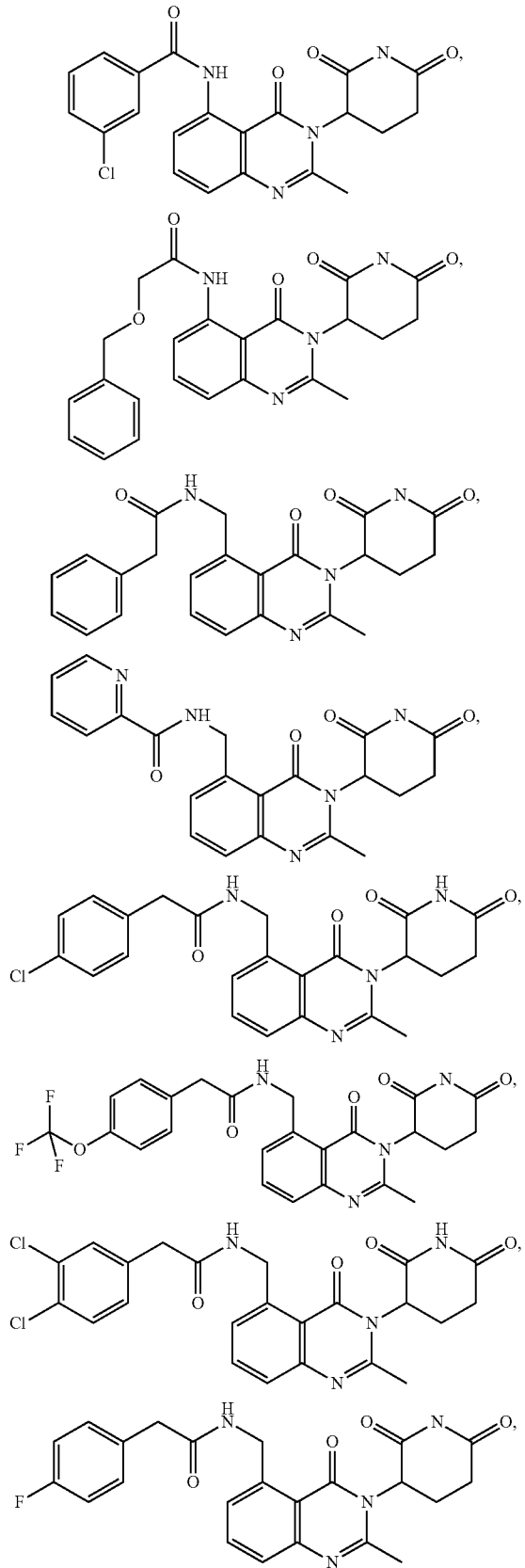
-continued
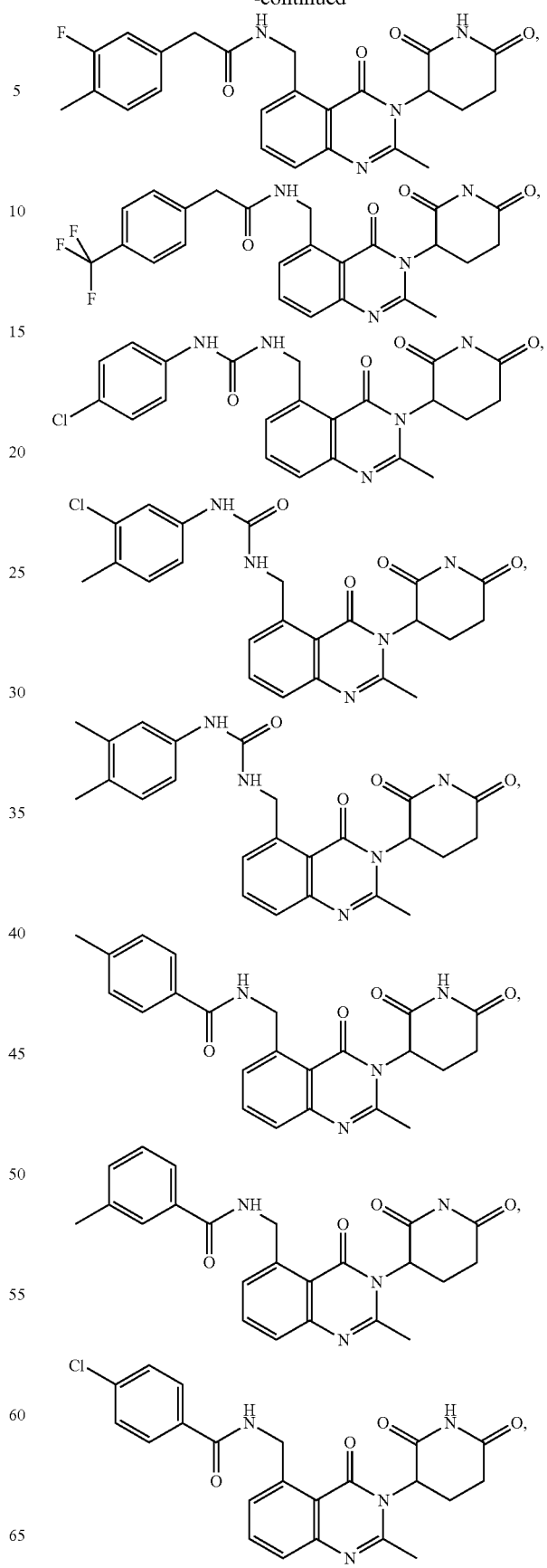

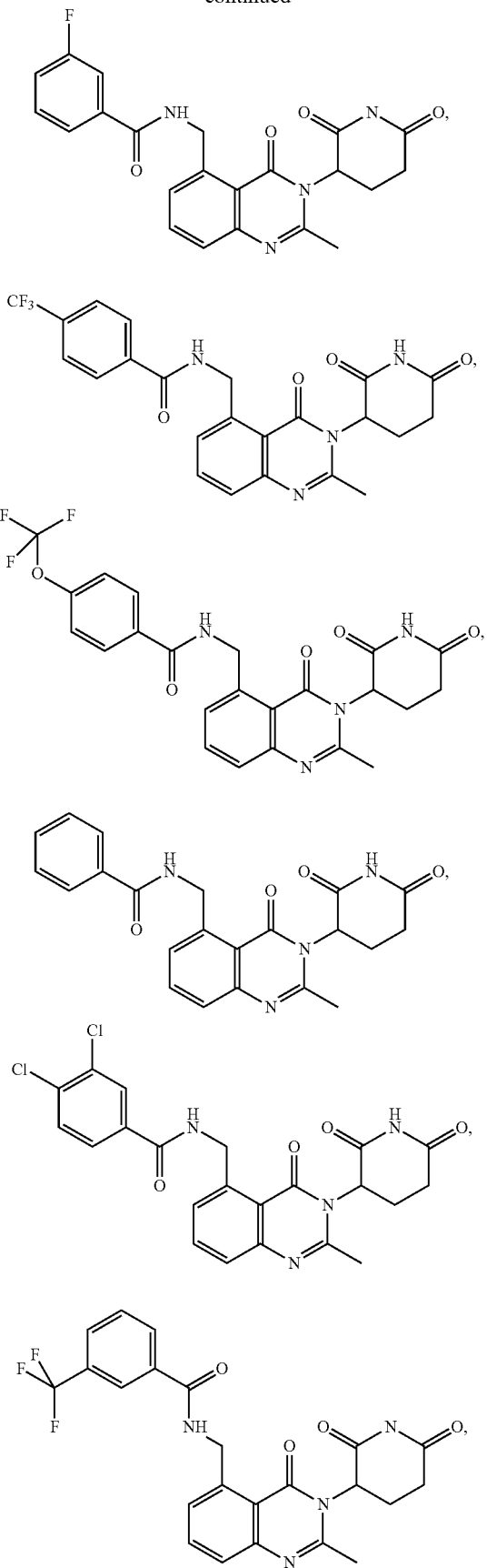

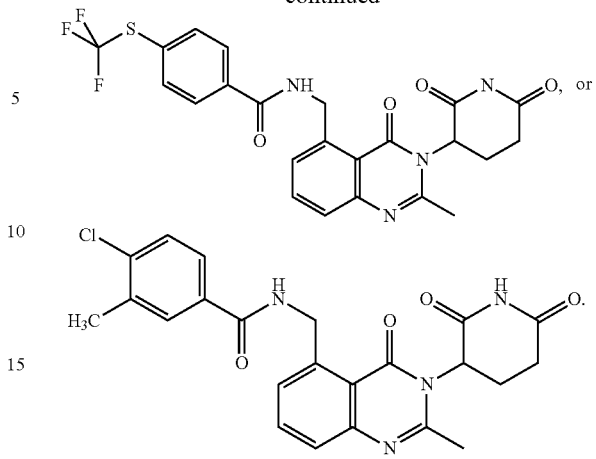

All of the compounds described herein can be either commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

Compounds provided herein may be small organic molecules having a molecular weight less than about 1,000 g/mol, and are not proteins, peptides, oligonucleotides, oligosaccharides, or other macromolecules.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

5.7 PHARMACEUTICAL COMPOSITIONS

In certain embodiments, provided herein are pharmaceutical compositions comprising a compound provided herein, e.g., lenalidomide. The pharmaceutical compositions provided herein contain therapeutically effective amounts of one or more of compounds provided herein and a pharmaceutically acceptable carrier, diluent or excipient. In some embodiments, the compounds may be formulated as the sole pharmaceutically active ingredient in the composition or may be combined with other active ingredients.

The compounds can be formulated into suitable pharmaceutical compositions for different routes of administration, such as oral, injection, sublingual and buccal, rectal, vaginal, ocular, otic, nasal, inhalation, nebulization, cutaneous, or transdermal. Typically the compounds described above are formulated into pharmaceutical compositions using techniques and procedures well known in the art (see, e.g., Ansel, *Introduction to Pharmaceutical Dosage Forms*, (7th ed. 1999)).

The compounds can be formulated into suitable pharmaceutical compositions for different routes of administration, such as oral, injection, sublingual and buccal, rectal, vaginal, ocular, otic, nasal, inhalation, nebulization, cutaneous, or transdermal. Typically the compounds described above are formulated into pharmaceutical compositions using techniques and procedures well known in the art (see, e.g., Ansel, *Introduction to Pharmaceutical Dosage Forms*, (7th ed. 1999)).

In the compositions, effective concentrations of one or more compounds or pharmaceutically acceptable salts are mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of cancer, including solid cancer and blood borne cancer.

The active compound is in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans. The concentration of active compound in the pharmaceutical composition will depend on absorption, tissue distribution, inactivation, and excretion rates of the active compound, the physicochemical characteristics of the compound, the dosage schedule, and amount administered as well as other factors known to those of skill in the art.

The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carriers, vehicles, or diluents. Examples of unit dose forms include ampoules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules, or bottles of pints or gallons. Hence, multiple dose form is a multiple of unit doses which are not segregated in packaging.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

For oral administration, a pharmaceutically acceptable non-toxic composition is formed by the incorporation of any of the normally employed excipients, for example, pharmaceutical grades of mannitol, lactose, starch, magnesium stearate, talcum, cellulose derivatives, sodium crosscarmellose, glucose, sucrose, magnesium carbonate, or sodium saccharin. Such compositions include solutions, suspensions, tablets, capsules, powders, sustained release formulations (such as, but not limited to, implants and microencapsulated delivery systems), and biodegradable, biocompatible polymers (such as collagen, ethylene vinyl acetate, polyanhydrides, polyglycolic acid, polyorthoesters, polylactic acid, and others). Methods for preparation of these compositions are known to those skilled in the art.

Solutions or suspensions used for parenteral, intradermal, subcutaneous, or topical application can include any of the following components: a sterile diluents (such as water, saline solution, fixed oil, polyethylene glycol, glycerine, propylene glycol, dimethyl acetamide, or other synthetic solvent), antimicrobial agents (such as benzyl alcohol and methyl parabens), antioxidants (such as ascorbic acid and sodium bisulfate), chelating agents (such as ethylenediaminetetraacetic acid (EDTA)), buffers (such as acetates, citrates, and phosphates), and agents for the adjustment of tonicity (such as sodium chloride or dextrose). Parenteral preparations can be enclosed in ampoules, pens, disposable syringes, or single or multiple dose vials made of glass, plastic, or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolving the compound in aqueous sodium hydroxide, sodium bicarbonate, or hydrochloric acid.

Sustained-release preparations can also be prepared. Suitable examples of sustained-release preparations include semipermeable matrices of solid hydrophobic polymers containing the compound provided herein, which matrices are in the form of shaped articles, e.g., films or microcapsule. Examples of sustained-release matrices include iontophoresis patches, polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Lactose-free compositions provided herein can contain excipients that are well known in the art and are listed, for example, in The U.S. Pharmacopeia (USP). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch, and magnesium stearate.

Further encompassed are anhydrous pharmaceutical compositions and dosage forms containing a compound provided herein. Anhydrous pharmaceutical compositions and dosage forms provided herein can be prepared using anhydrous or low moisture containing ingredients and low moisture or low humidity conditions, as known by those skilled in the art. An anhydrous pharmaceutical composition should be prepared and stored such that its anhydrous nature is maintained. Accordingly, anhydrous compositions are packaged using materials known to prevent exposure to water such that they can be included in suitable formulatory kits. Examples of suitable packaging include, but are not limited to, hermetically sealed foils, plastics, unit dose containers (e.g., vials), blister packs, and strip packs.

Dosage forms or compositions containing active ingredient in the range of 0.001% to 100% with the balance made up from non-toxic carrier may be prepared. In some embodiments, the contemplated compositions contain from about 0.005% to about 95% active ingredient. In other embodiments, the contemplated compositions contain from about 0.01% to about 90% active ingredient. In certain embodiments, the contemplated compositions contain from about 0.1% to about 85% active ingredient. In other embodiments, the contemplated compositions contain from about 0.1% to about 75-95% active ingredient.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to herein above, such as solid cancer or blood born cancer. It is to be understood that such combination therapy constitutes a further aspect of the compositions and methods of treatment provided herein.

5.7.1 Oral Dosage Forms

Oral pharmaceutical dosage forms are either solid, gel, or liquid. The solid dosage forms are tablets, capsules, granules, and bulk powders. Types of oral tablets include compressed, chewable lozenges, and tablets, which may be enteric coated, sugar coated, or film coated. Capsules may be hard or soft gelatin capsules, while granules and powders may be provided in non-effervescent or effervescent form with the combination of other ingredients known to those skilled in the art.

In certain embodiments, the formulations are solid dosage forms, such as capsules or tablets. The tablets, pills, capsules, troches, and the like, can contain any one or combination of the following ingredients, or compounds of a similar nature: a binder, a diluents, a lubricant, a glidant, a disintegrating agent, a coloring agent, a sweetening agent, a flavoring agent, a wetting agent, and a coating (e.g., an enteric coating or a film coating).

Examples of binders include microcrystalline cellulose, gum tragacanth, glucose solution, acacia mucilage, gelatin solution, sucrose, and starch paste. Diluents include, for example, lactose, sucrose, starch, kaolin, salt, mannitol, and dicalcium phosphate. Lubricants include, for example, talc, starch, magnesium or calcium stearate, lycopodium, and stearic acid. Glidants include, but are not limited to, colloidal silicon dioxide. Disintegrating agents include, for example, crosscarmellose sodium, sodium starch glycolate, alginic acid, corn starch, potato starch, bentonite, methylcellulose, agar, and carboxymethylcellulose. Coloring agents include, for example, any of the approved certified water soluble FD and C dyes, mixtures thereof, and water insoluble FD and C dyes suspended on alumina hydrate. Sweetening agents include, for example, sucrose, lactose, mannitol, artificial sweetening agents such as saccharin, and any number of spray dried flavors. Flavoring agents include, for example, natural flavors extracted from plants such as fruits, and synthetic blends of compounds, which produce a pleasant sensation, including but not limited to peppermint and methyl salicylate. Wetting agents include, for example, propylene glycol monostearate, sorbitan monooleate, diethylene glycol monolaurate, and polyoxyethylene laural ether. Enteric coatings include, for example, fatty acids, fats, waxes, shellac, ammoniated shellac, and cellulose acetate phthalates. Film coatings include, for example, hydroxyethylcellulose, sodium carboxymethylcellulose, polyethylene glycol 4000, and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Liquid oral dosage forms include aqueous solutions, emulsions, suspensions, solutions, and/or suspensions reconstituted from non-effervescent granules and effervescent preparations reconstituted from effervescent granules. Aqueous solutions include, for example, elixirs and syrups. Emulsions are either oil-in-water or water-in-oil. Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents, and preservatives. Suspensions use pharmaceutically acceptable suspending agents and preservatives. Pharmaceutically acceptable substances used in non-effervescent granules, to be reconstituted into a liquid oral dosage form, include diluents, sweeteners, and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol, and syrup. Examples of preservatives include glycerin, methyl and propylparaben, benzoic add, sodium benzoate, and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum, and acacia. Diluents include lactose and sucrose. Sweetening agents include sucrose, syrups, glycerin, and artificial sweetening agents such as saccharin. Wetting agents include propylene glycol monostearate, sorbitan monooleate, diethylene glycol monolaurate, and polyoxyethylene lauryl ether. Organic acids include citric and tartaric acid. Sources of carbon dioxide include sodium bicarbonate and sodium carbonate.

For a solid dosage form, the solution or suspension in, for example, propylene carbonate, vegetable oils, or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate), and other such carriers, and encapsulating these solutions or suspensions in hard or soft gelatin capsule shells. Other useful formulations include, but are not limited to, those containing a compound provided herein, a dialkylated mono- or poly-alkylene glycol, including but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

5.7.2 Injectables, Solutions, and Emulsions

Parenteral administration of the compositions includes intravenous, subcutaneous, and intramuscular administrations. Compositions for parenteral administration include sterile solutions ready for injection, sterile dry soluble products, such as lyophilized powders, ready to be combined with a solvent just prior to use, sterile suspensions ready for injection, and sterile emulsions. The solutions may be either aqueous or nonaqueous. The unit dose parenteral preparations are packaged in an ampoule, a vial or a syringe with a needle. All preparations for parenteral administration must be sterile, as is known and practiced in the art.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents, and other pharmaceutically acceptable substances.

Examples of aqueous vehicles include sodium chloride injection, Ringer's injection, isotonic dextrose injection, sterile water injection, dextrose and lactated Ringer's injection. Nonaqueous parenteral vehicles include fixed oils of vegetable origin, such as cottonseed oil, corn oil, sesame oil, and peanut oil. Antimicrobial agents in bacteriostatic or fungistatic concentrations must be added to parenteral preparations packaged in multiple dose containers, which include phenols or cresols, mercurials, benzyl alcohol, chlorobutanol, methyl and propyl-p-hydroxybenzoic acid esters, thimerosal, benzalkonium chloride, and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles, and sodium hydroxide, hydrochloric acid, citric acid, or lactic acid for pH adjustment.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

5.7.3 Lyophilized Powders

Of interest herein are also lyophilized powders, which can be reconstituted for administration as solutions, emulsions, and other mixtures. They may also be reconstituted and formulated as solids or gels.

The sterile, lyophilized powder is prepared by dissolving a compound provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose, or other suitable agent. The solvent may also contain a buffer, such as citrate, phosphate, or other buffers known to those of skill in the art. In one embodiment, the buffer has a pH about neutral. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per milliliter of sterile water or other suitable carrier. The precise amount depends upon the selected compound. Such amount can be empirically determined.

5.7.4 Topical Administration

Topical mixtures are prepared as described for the local and systemic administration. The resulting mixture may be a solution, suspension, emulsion, or the like and are formulated as creams, gels, ointments, emulsions, solutions, elixirs, lotions, suspensions, tinctures, pastes, foams, aerosols, irrigations, sprays, suppositories, bandages, dermal patches, or any other formulations suitable for topical administration.

The compounds or pharmaceutically acceptable salts thereof may be formulated as aerosols for topical application, such as by inhalation (see, e.g., U.S. Pat. Nos. 4,044, 126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

These solutions, particularly those intended for ophthalmic use, may be formulated as 0.01%-10% isotonic solutions, pH about 5-7, with appropriate salts.

5.7.5 Compositions for Other Routes of Administration

Other routes of administration such as transdermal patches and rectal administration are also contemplated herein.

For example, pharmaceutical dosage forms for rectal administration are rectal suppositories, capsules, and tablets for systemic effect. Rectal suppositories as used herein mean solid bodies for insertion into the rectum, which melt or soften at body temperature releasing one or more pharmacologically or therapeutically active ingredients. Pharmaceutically acceptable substances utilized in rectal suppositories include bases (or vehicles) and agents that raise the melting point. Examples of bases include, for example, cocoa butter (*theobroma* oil), glycerin gelatin, carbowax (polyoxyethylene glycol), and appropriate mixtures of mono, di and triglycerides of fatty acids. Combinations of the various bases may be used. Agents to raise the melting point of suppositories include, for example, spermaceti and wax. Rectal suppositories may be prepared either by the compressed method or by molding. An exemplary weight of a rectal suppository is about 2 to 3 grams.

Tablets and capsules for rectal administration are manufactured using the same pharmaceutically acceptable substance and by the same methods as for formulations for oral administration.

5.7.6 Sustained Release Compositions

Active ingredients provided herein can be administered by controlled release means or by delivery devices that are well known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500, and 6,740,634, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side effects (e.g., adverse effects).

Most controlled-release formulations are designed to initially release an amount of drug (active ingredient) that promptly produces the desired therapeutic effect, then to gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, other physiological conditions, or compounds.

In certain embodiments, the agent may be administered using intravenous infusion, an implantable osmotic pump, a transdermal patch, liposomes, or other modes of administration. In one embodiment, a pump may be used. See, Sefton, *CRC Crit. Ref. Biomed. Eng.* 1987, 14:201-240; Buchwald et al., *Surgery* 1980, 88:507-516; Saudek et al., *N. Engl. J. Med.* 1989, 321:574-579. In another embodiment, polymeric materials can be used. In yet another embodiment, a controlled release system can be placed in proximity of the therapeutic target, thus requiring only a fraction of the systemic dose. See, e.g., Goodson, *Medical Applications of Controlled Release*, vol. 2, pp. 115-138 (1984).

In some embodiments, a controlled release device is introduced into a subject in proximity of the site of inappropriate immune activation or a tumor. Other controlled release systems are discussed in the review by Langer (*Science* 1990, 249:1527-1533). The active ingredient can be dispersed in a solid inner matrix (e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate). In some embodiments, the inner matrix is surrounded by an outer polymeric membrane (e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene, propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer). In certain embodiments, the outer polymeric membrane is insoluble in body fluids. The active ingredient then diffuses through the outer polymeric membrane in a release rate controlling step. The percentage of active ingredient contained in such parenteral compositions depends on the specific nature thereof, as well as the needs of the subject.

5.7.7 Targeted Formulations

The compounds provided herein, or pharmaceutically acceptable salts thereof, may also be formulated to target a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542, and 5,709,874.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLVs) may be formed by drying down egg phosphatidyl choline and brain phosphatidyl serine (7:3 molar ratio) on the inside of a flask. A solution of a compound provided herein in phosphate buffered saline (PBS) lacking divalent cations is added, and the flask is shaken until the lipid film is dispersed. The resulting vesicles are washed to remove unencapsulated compound, pelleted by centrifugation, and then resuspended in PBS.

5.7.8 Articles of Manufacture

The compounds or pharmaceutically acceptable salts can be packaged as articles of manufacture containing packaging material, a compound or pharmaceutically acceptable salt thereof provided herein, which is used for treatment, prevention, or amelioration of one or more symptoms or progression of cancer, including solid cancers and blood borne tumors, and a label indicating that the compound or pharmaceutically acceptable salt thereof is used for treatment, prevention, or amelioration of one or more symptoms or progression of cancer, including solid cancers and blood borne tumors.

The articles of manufacture provided herein contain packaging materials. Packaging materials for use in packaging pharmaceutical products are well known to those of skill in the art. See, e.g., U.S. Pat. Nos. 5,323,907, 5,052,558, and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

5.8 KITS FOR DETECTING BIOMARKER LEVELS

In certain embodiments, provided herein is a kit for performing the various methods provided herein.

For example, in some embodiments, provided herein is a kit for identifying a subject having a cancer who is likely to be responsive to a treatment compound, comprising:
(a) an agent for determining the level of a first biomarker; and
(b) an agent for determining the level of a second biomarker,
wherein at least one of the biomarkers is a CRBN-associated protein.

In some embodiments, provided herein is a kit for predicting the responsiveness of a subject having or suspected of having a cancer to a treatment compound, comprising:
(a) an agent for determining the level of a first biomarker; and
(b) an agent for determining the level of a second biomarker,
wherein at least one of the biomarkers is a CRBN-associated protein.

In other embodiments, provided herein is a kit for monitoring the efficacy of a treatment of a cancer in a subject with a treatment compound, comprising:
(a) an agent for determining the level of a first biomarker; and
(b) an agent for determining the level of a second biomarker,
wherein at least one of the biomarkers is a CRBN-associated protein.

In some embodiments, the cancer is a leukemia. In some embodiments, the cancer is a lymphoma. In other embodiments, the cancer is an Adult T-cell Leukemia (ATL). In other embodiments, the cancer is relapsed, refractory or resistant to conventional therapy. In other embodiments, the cancer is a relapsed or refracted ATL.

In some embodiments, the treatment compound is an immunomodulatory compound. In some embodiments, the treatment compound is lenalidomide.

In a specific embodiment, the treatment compound is lenalidomide and the cancer is ATL.

In some embodiments, the first biomarker is selected from the group comprising CRBN, IKZF1, and IKZF2. In some embodiments, the second biomarker is selected from the group comprising CRBN, IKZF1, and IKZF2. In some embodiments, the first biomarker and the second biomarker are selected from the group comprising CRBN, IKZF1, and IKZF2.

In some embodiments, the first biomarker is CRBN. In some embodiments, when the first biomarker is CRBN, the second biomarker is a substrate of CRBN. In other embodiments, when the first biomarker is CRBN, the second biomarker is not a substrate of CRBN.

In some embodiments, the first biomarker is CRBN and the second biomarker is IKZF1. In some embodiments, the ratio of the CRBN expression level to the IKZF1 expression level is higher than 3. In other embodiments, the ratio of the CRBN expression level to the IKZF1 expression level is higher than 4. In yet other embodiments, the ratio of the CRBN expression level to the IKZF1 expression level is higher than 5.

In other embodiments, the first biomarker is CRBN and the second biomarker is IKZF2. In some embodiments, the ratio of the CRBN expression level to the IKZF2 expression level is between 500 and 5000. In other embodiments, the ratio of the CRBN expression level to the IKZF2 expression level is higher than 500. In other embodiments, the ratio of the CRBN expression level to the IKZF2 expression level is higher than 1000. In yet other embodiments, the ratio of the CRBN expression level to the IKZF2 expression level is higher than 1500. In yet other embodiments, the ratio of the CRBN expression level to the IKZF2 expression level is higher than 2500.

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an organ, an organelle, a biological fluid, a blood sample, a urine sample, or a skin sample.

In another embodiment, the kit comprises a solid support, nucleic acids attached to the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray In certain embodiments, the kits provided herein employ means for detecting the expression of a biomarker by quantitative real-time PCR (qRT-PCR), microarray, flow cytometry, or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring biomarkers that supply the materials necessary to measure the abundance of one or more gene products of the biomarkers or a subset of the biomarkers (e.g., one, two, three, four, five, or more biomarkers) provided herein. Such kits may comprise materials and reagents required for measuring RNA or protein. In some embodiments, such kits include microarrays, wherein the microarray is comprised of oligonucleotides and/or DNA and/or RNA fragments which hybridize to one or more gene products of the biomarkers or a subset of the biomarkers provided herein, or any combination thereof. In some embodiments, such kits may include primers for PCR of either the RNA product or the cDNA copy of the RNA product of the biomarkers or a subset of the biomarkers, or both. In some embodiments, such kits may include primers for PCR as well as probes for qPCR. In some embodiments, such kits may include multiple primers and multiple probes, wherein some of the probes have different fluorophores so as to permit simultaneously measuring multiple gene products of the biomarkers or a subset of the biomarkers provided herein. In some embodiments, such kits may further include materials and reagents for creating cDNA from RNA. In some embodiments, such kits may include antibodies specific for the protein products of the biomarkers or a subset of the biomarkers provided herein. Such kits may additionally comprise materials and reagents for isolating RNA and/or proteins from a biological sample. In addition, such kits may include materials and reagents for synthesizing cDNA from RNA isolated from a biological sample. In some embodiments, such kits may include a computer program product embedded on computer readable media for predicting whether a patient is clinically sensitive to a compound. In some embodiments, the kits may include a computer program product embedded on a computer readable media along with instructions.

In some embodiments, such kits measure the expression of one or more nucleic acid products of the biomarkers or a subset of the biomarkers provided herein. In accordance with this embodiment, the kits may comprise materials and reagents that are necessary for measuring the expression of particular nucleic acid products of the biomarkers or a subset of the biomarkers provided herein. For example, a microarray or RT-PCR kit may be produced for a specific condition and contain only those reagents and materials necessary for measuring the levels of specific RNA transcript products of the biomarkers or a subset of the biomarkers provided herein, to predict whether a hematological cancer in a patient is clinically sensitive to a compound. Alternatively, in some embodiments, the kits can comprise materials and reagents necessary for measuring the expression of particular nucleic acid products of genes other than the biomarkers provided herein. For example, in certain embodiments, the kits comprise materials and reagents necessary for measuring the expression levels of 1, 2, 3, or more of the genes of the biomarkers provided herein, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than the biomarkers provided herein. In other embodiments, the kits contain reagents and materials necessary for measuring the expression levels of at least 1, at least 2, at least 3, or more of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not the biomarkers provided herein. In certain embodiments, the kits contain reagents and materials necessary for measuring the expression levels of at least 1, at least 2, at least 3, or more of the genes of the biomarkers provided herein, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not the biomarkers provided herein.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from performing the assay. In a specific embodiment, the kits comprise instructions for predicting whether a hematological cancer in a patient is clinically sensitive to a compound. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own suitable container.

In certain embodiments, a nucleic acid microarray kit comprises materials and reagents necessary for measuring the expression levels of 1, 2, 3, or more of the genes of the biomarkers provided herein, or a combination thereof, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than those of the biomarkers provided herein. In other embodiments, a nucleic acid microarray kit contains reagents and materials necessary for measuring the expression levels of at least 1, at least 2, at least 3, or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein. In another embodiment, a nucleic acid microarray kit contains reagents and materials necessary for measuring the expression levels of at least 1, at least 2, at least 3, or more of the genes of the biomarkers provided herein, or any combination thereof, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, or 500-1000 genes that are not of the biomarkers provided herein.

For quantitative PCR, the kits generally comprise preselected primers specific for particular nucleic acid sequences. The quantitative PCR kits may also comprise enzymes suitable for amplifying nucleic acids (e.g., polymerases such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In some embodiments, the quantitative PCR kits also comprise components suitable for reverse-transcribing RNA, including enzymes (e.g., reverse transcriptases such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction. In a specific embodiment, the kits contain instructions for predicting whether a hematological cancer in a patient is clinically sensitive to a compound.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). In a specific embodiment, the peptide, polypeptide, or protein of interest is associated with or indicative of a condition (e.g., a disease). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay. In a specific embodiment, the kits contain instructions for predicting whether a hematological cancer in a patient is clinically sensitive to a compound.

In one embodiment, a kit provided herein comprises a compound provided herein, or a pharmaceutically acceptable salt, solvate, or hydrate thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation, as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to, water for injection USP; aqueous vehicles (such as, but not limited to, sodium chloride injection, Ringer's injection, dextrose injection, dextrose and sodium chloride injection, and lactated Ringer's injection); water-miscible vehicles (such as, but not limited to, ethyl alcohol, polyethylene glycol, and polypropylene glycol); and non-aqueous vehicles (such as, but not limited to, corn oil, cottonseed oil, peanut oil, sesame oil, ethyl oleate, isopropyl myristate, and benzyl benzoate).

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

6. EXAMPLES

The examples below are carried out using standard techniques, which are well known and routine to those of skill in the art, except where otherwise described in details. The examples are intended to be merely illustrative.

6.1 Example 1—Preparation of 3-(4-amino-1-oxo-1,3-dihydro-isoindol-2-yl)-piperidine-2,6-dione (lenalidomide)

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered, and the solid was washed with methylene chloride (50 mL). The filtrate was washed with water (2×100 mL), brine (100 mL), and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$ (aq) 7.27 min(98.92%); Anal. Calcd for C$_9$H$_8$NO$_4$Br: C, 39.44; H, 2.94; N, 5.11; Br, 29.15. Found: C, 39.46; H, 3.00; N, 5.00; Br, 29.11.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL), and dried. The solvent was removed in vacuo and the residue was purified by flash chromatography (3% CH$_3$OH in methylene chloride) to afford 2.84 g (60%) of crude product, which was used directly in the next reaction: 1H NMR (CDCl$_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 CH$_3$CN/0.1% H$_3$PO$_4$ (aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether, and dried to afford 3.3 g of the product: 1H NMR (DMSO-d$_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 amd 10.4 Hz, 1H), 2.34-2.10 (m, 4H); $^{13}$C NMR (DMSO-d$_6$) δ 173.03, 171.88, 165.96, 143.35, 137.49, 134.77, 130.10, 129.61, 126.95, 53.65, 48.13, 31.50, 24.69; Anal. Calcd for C$_{13}$H$_{13}$N$_3$O$_6$: C, 50.82; H, 4.26; N, 13.68. Found: C, 50.53; H, 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 1 1.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL), and dried. The solvent was removed in vacuo and the solid residue was slurried with ethyl acetate (20 mL) to give 2.2 g (75%) of the product as a white solid: mp 285° C.; 1H NMR (DMSO-d$_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-d$_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 CH$_3$CN/0.1% H$_3$PO$_4$ (aq) 3.67 min(100%); Anal. Calcd for C$_{13}$H$_n$N$_3$O$_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered, and dried to afford 0.46 g (51%) of the product as a white solid: mp 235.5-239° C.; $^1$H NMR (DMSO-d$_6$) δ 11.01 (s, 1H). 7.19 (t, J=7.6 Hz, 1H). 6.90 (d, J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}$C NMR (DMSO-d$_6$) δ 172.85, 171.19, 168.84, 143.58, 132.22. 128.79, 125.56, 1 16.37, 1 10.39, 51.48, 45.49, 31.20, 22.74; HPLC. Waters Nova-Pak/C18, 3.9×150 mm, 4 micron, 1 mL/min, 240 nm, 10/90 CH$_3$CN/0.1% H$_3$PO$_4$ (aq) 0.96 min(100%); Chiral analysis, Daicel Chiral Pak AD, 40/60 Hexane/IPA, 6.60 min(99.42%); Anal. Calcd for C$_{13}$H$_{13}$N$_3$O$_3$: C, 60.23; H, 5.05; N, 16.21. Found: C, 59.96; H, 4.98; N, 15.84.

3-(4-Amino-1-oxo-1,3-dihydro-isoindol-2-yl)-piperidine-2,6-dione may also be prepared by methods known in the art, for example, as provided in *Treatment compounds of the Future* 2003, 28(5):425-431, the entirety of which is incorporated by reference.

6.2 Example 2—High mRNA Expression Level Ratio of CRBN to IKZF1 or IKZF2 Correlates with Lenalidomide-Responsive ATL Cells Twenty-three types of cells from, e.g., ATL cell lines, lymphoma cell lines, leukemia cell lines, healthy peripheral blood mononuclear cells (PBMCs), and human T-lymphotropic virus 1 (HTLV-1) carrier's PBMCs are employed in this example. Among these types of cells, cell line 5 is a lenalidomide-highly-sensitive ATL cell line; cell lines 6 and 12 are lenalidomide-weak/moderate-sensitive ATL cell lines; and other cell lines (cell lines 1-4, 7, 10-11, and 13-23) exhibit intense tolerance to lenalidomide.

mRNAs of CRBN, IKZF1 (Ikaros), IKZF2 (Helios) and IKZF3 (Aiolos) from each type of cells were extracted and quantitated by qPCR, and the ratio of CRBN mRNA expression level to IKZF1 mRNA expression level, and the ratio of CRBN mRNA expression level to IKZF2 mRNA expression level were calculated. The results are shown in FIG. 2A (CRBN/IKZF1) and FIG. 2B (CRBN/IKZF2).

Figure 2A:
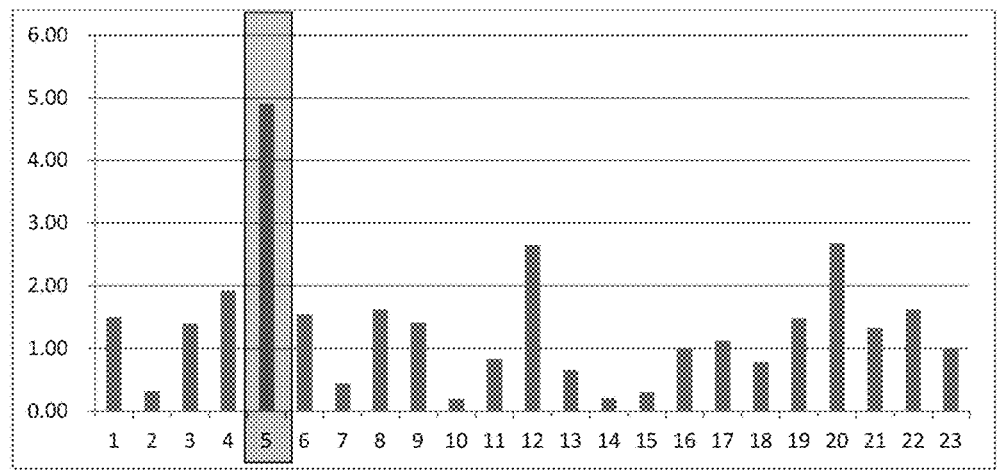
FIGS. 2A-2B show the ratios of mRNA expression levels of CRBN to IKZF1 (FIG. 2A) and CRBN to IKZF2 (FIG. 2B) in different types of cells.
Figure 2B:
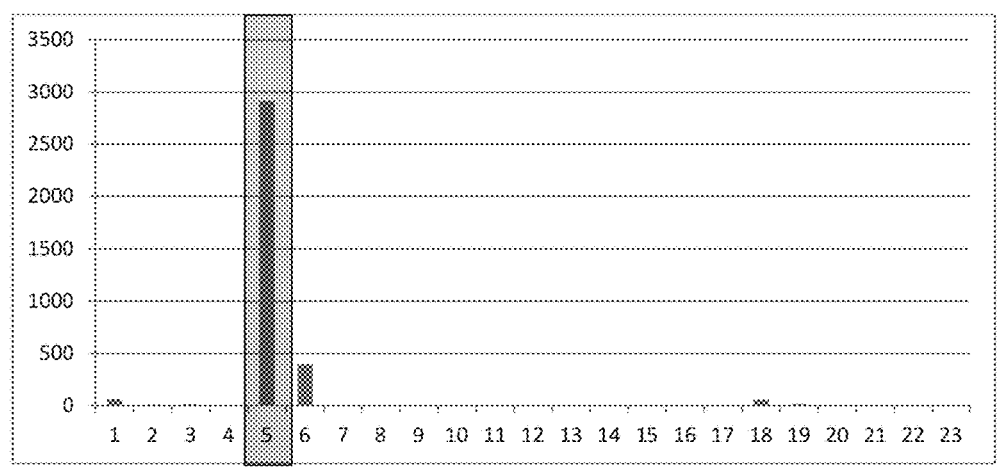

As shown in FIGS. 2A-2B, the lenalidomide-highly-sensitive ATL cell line—cell line 5—exhibits much higher ratio of CRBN to IKZF1 and CRBN to IKZF2. It is interesting that IKZF2 is a class of IKZF family, but not a CRBN substrate. Based on these results, an examination of CRBN/IKZF1 ratio and/or CRBN/IKZF2 ratio can be used to detect lenalidomide-responsive ATL patients.

6.3 Example 3—Lenalidomide Exhibits Various Proliferation Inhibitory Effects on Different ATL Cell Lines Ten ATL-patient derived cell lines, three HTLV-1 transformed cell lines, five HTLV-1 negative T-cell or monocyte malignant cell lines, and two multiple myeloma cell lines (NCI-H929 as responsive and RPMI-8226 as irresponsive controls) were selected for lenalidomide efficacy study. ATL cell lines Hut102, ED40515, S1T, OATL4, and OATL9, HTLV-1 transformed cell lines MT-2, MT-4, and C8166, PTCL cell line Hut78, other T-cell Jurkat, MOLT4, HL60, and monocyte cell line K562 are laboratory stocks (Dr. Hidekatsu Iha, Oita University, and Prof. Kazuhiro Morishita, The University of Miyazaki). ATL cell lines ST1, KOB, KK1, and SO4 are gift from Dr. Hiroo Hasegawa, Nagasaki University). NCI-H929 and RPMI-8226 were purchased from American Type Culture Collection (ATCC: Manassas, Va.). Each cell line was maintained with RPMI-1640 culture media supplemented with 15% fetal bovine serum (FBS: Equitech-Bio Inc., Kerrville, Tex.), penicillin G (50 U/ml), and streptomycin (50 µg/ml). Antibiotics were purchased from Sigma-Aldrich Co. LLC. (St. Louis, Mo.). Characteristics of cell lines used for this study are shown in Table 1 below.

Cells were plated in 24-well plates at $5 \times 10^4$ cells per 1.5 mL RPMI1640 and kept in 5% $CO_2$ incubator for 24 hours (cell number should reach $1 \times 10^5$). Before (day 0) or after (day 1, 2, 3) addition of lenalidomide (7.5 µL, 200× concentration each) to the cultured media, approximately 800 cells in 12.5 µL media were harvested and mixed with equal volume of CellTiter solution (Promega) for each assay (triplicated). After 10 minutes incubation at room temperature, the reaction mixture in 96-well plates was read by Glomax luminometer (Promega). Average values and standard deviation were obtained from four independent experiments.

TABLE 1

Characteristics of cell lines used for the study

| Name | Origin | Cell Lineage | Tax expression | Infectivity |
|---|---|---|---|---|
| RPMI-8226 | MM*1 | Plasma/B-cell | — | — |
| NCI-H929 | | | | |
| Hut102 | ATL*2 | T-cell | Yes | Yes |

TABLE 1-continued

Characteristics of cell lines used for the study

| Name | Origin | Cell Lineage | Tax expression | Infectivity |
|---|---|---|---|---|
| ED40515 | | | No | No |
| Su9T1 | | | | |
| OATL4 | | | Yes | ND* |
| OATL9 | | B-cell | | |
| S1T | | T-Cell | No | No |
| ST1 | | | | |
| KOB | | | Yes | ND |
| KK1 | | | No | No |
| SO4 | | | | |
| MT-2 | HTLV-1 | T-cell | Yes | Yes |
| MT-4 | Transformed | | | |
| C8166 | cord blood | Lymphoblast | | No |
| HuT78 | SS/CTCL*3 | T-cell | — | — |
| MOLT4 | ALL*4 | T-lymphoblastic | | |
| Jurkat | ATCL*5 | Lymphoblast | | |
| K562 | CML*6 | | | |
| HL60 | APML*7 | Promyelocytic | | |

*1Multiple Myeloma
*2Adult T-cell Leukemia Lymphoma
*3Sezary Syndrome/Cutaneous T-cell Lymphoma
*4Acute T-Lymphoblastic Leukemia
*5Acute T-cell Leukemia
*6Chronic Myelogeneous Leukemia
*7Acute Promyelocytic Leukemia
*Not Determined Relative CellTiter values compared to untreated control cells at day 0 were plotted. As shown in FIG. 3, two multiple myeloid control cell lines NCI-H929 and RPMI-8226 display sensitive and insensitive responses against lenalidomide treatment, respectively. Among 13 ATL-related cell lines, Hut102 cell exhibits significant decrease of cell proliferation activity (remaining activities at 0.1 µM lenalidomide treatment: 64.2% (p=0.0468); at 1 µM lenalidomide treatment: 68.3% (p=0.2443); at 10 µM lenalidomide treatment: 46.0% (p=0.0285); and at 100 µM lenalidomide treatment: 53.0% (p=0.0307)). In addition, OATL4 and KOB display 30% more reductions (see Table 2).

TABLE 2

Remaining cell proliferation activities after three day treatment of lenalidomide
Relative Cell Titer Values @Day 3 (vs Day 0/Control)

| Name | 0 | 0.1 | 1 | 10 | 100 |
|---|---|---|---|---|---|
| RPMI-8226 | 1.00 | 1.09 | 1.20 | 0.76 | 0.80 |
| NCI-H929 | 1.00 | 0.54 | 0.23 | 0.14 | 0.14 |
| Hut102 | 1.00 | 0.64 | 0.68 | 0.46 | 0.53 |
| ED40515 | 1.00 | 1.05 | 0.95 | 0.88 | 0.95 |
| Su9T1 | 1.00 | 1.05 | 1.67 | 0.88 | 0.87 |
| OATL4 | 1.00 | 0.68 | 0.90 | 0.78 | 0.80 |
| OATL9 | 1.00 | 0.75 | 0.91 | 0.98 | 0.76 |
| S1T | 1.00 | 1.10 | 1.24 | 1.35 | 1.39 |
| ST1 | 1.00 | 1.15 | 1.25 | 1.14 | 1.15 |
| KOB | 1.00 | 1.20 | 0.83 | 0.68 | 0.73 |
| KK1 | 1.00 | 0.96 | 1.14 | 1.07 | 1.12 |
| SO4 | 1.00 | 1.01 | 0.99 | 1.00 | 1.08 |
| MT-2 | 1.00 | 1.05 | 0.79 | 0.82 | 0.80 |
| MT-4 | 1.00 | 0.87 | 0.89 | 0.86 | 0.77 |
| C8166 | 1.00 | 1.17 | 1.09 | 0.98 | 0.94 |
| HuT78 | 1.00 | 0.97 | 0.88 | 0.95 | 0.97 |
| MOLT4 | 1.00 | 0.82 | 0.84 | 1.03 | 0.73 |
| Jurkat | 1.00 | 0.97 | 1.16 | 1.05 | 1.08 |
| K562 | 1.00 | 0.88 | 0.85 | 0.72 | 0.92 |
| HL60 | 1.00 | 0.81 | 0.88 | 0.86 | 0.90 |

6.4 Example 4—Proliferation Inhibitory Effects of Lenalidomide on Sensitive ATL Cell Line is Time-Dependent In addition to dose-dependent effects, lenalidomide also suppresses proliferation of Hut102 cells in a time-dependent manner. The remaining growth activities were compared between HuT102 (lenalidomide-sensitive) and HuT78 (lenalidomide-insensitive) with treatment of 10 µM lenalidomide for three days. The CellTiter Assay was performed the same way as in Section 6.3, Example 3. Standard deviation was calculated from four experiments. As shown in FIG. 4, while HuT102 exhibits significant decrease in cell growth over the three-day period, the values for HuT78 remains almost unchanged.

6.5 Example 5—The mRNA Expression Level Ratio of CRBN to IKZF1 and CRBN to IKZF2 Correlates with the Sensitivity of the ATL Cell Line to Lenalidomide The mRNA expression profile of the potential lenalidomide target genes in the above-tested cell lines (Section 6.3, Example 3) was measured using Real-Time PCR. Cells with or without lenalidomide treatment were harvested, and total RNAs were prepared by RNeasy kit (QIAGEN) for Real-Time PCR analysis. Universal Probe Library and Light Cycler 480 system were employed for quantitative mRNA expression analysis (Roche).

The levels of CRBN, IKZF1, IKZF2, and IKZF3 were analyzed. The anticipated expression profiles were observed as follows: 1) High CRBN expression in lenalidomide-sensitive cells and low CRBN expression in lenalidomide-insensitive cells; 2) Low expression of IKZF families in lenalidomide-sensitive cells and high expression of IKZF families in lenalidomide-insensitive cells (FIGS. 5A-5C). FIG. 5A represents relative expression ratios of CRBN and IKZF1 (CRBN/IKZF1) in each cell. As shown in FIG. 5A, lenalidomide-sensitive NCI-H929 and HuT102 cells both show higher ratios of CRBN/IKZF1 than other cells that are less sensitive to lenalidomide. KOB and MOLT-4 cells that are moderately sensitive to lenalidomide (30% growth inhibition, see Table 2) also show relatively high ratios of CRBN/IKZF1. All these ratios are higher than healthy or carrier CD4 controls. FIG. 5B represents relative expression ratios of CRBN and IKZF3 (CRBN/IKZF3) in each cell. No significant correlation between the ratio of CRBN/IKZF3 and lenalidomide-sensitivity was observed. In particular, the high ratio shown in HL60 cells is due to significantly decreased IKZF3 expression in those cells (FIG. 5B). FIG. 5C represents relative expression ratios of CRBN and IKZF2 (CRBN/IKZF2) in each cell. Lenalidomide-sensitive HuT102 cells show higher ratios of CRBN/IKZF2 than other cells. In addition, significantly decreased expression of IKZF2 in lenalidomide-sensitive HuT102 and moderate sensitive MT-4 was observed (FIG. 5C).

6.6 Example 6—Lenalidomide Induces Degradation of IKZF Family Proteins in Lenalidomide-Sensitive HuT102 Cells The protein expression profiles of HuT102 (lenalidomide-sensitive) and HuT78 (lenalidomide-insensitive) cells with or without lenalidomide treatment were analyzed using Western blotting. Three to five million cells were prepared and lysed with HEPES (pH7.3)/NP40 0.5% cell lysis buffer supplemented with protease inhibitor mix (Roche Diagnostics, Indianapolis, Ind.). Rabbit monoclonal antibodies against CRBN, IKZF1, IKZF2, and IKZF3 were purchased from Cell Signaling Technology (Danvers, Mass.), and mouse monoclonal anti-Tubulin antibody was from Sigma (St. Louis, Mo.).

As shown in FIG. 6, the basal protein amount of CRBN is much higher in HuT102 than HuT78, and the basal IKZF1 and IKZF2 protein levels are lower in HuT102 than HuT78. After three-day treatment with lenalidomed, in lenalidomide-sensitive HuT102 cells, IKZF1 disappears completely and IKZF3 decreases significantly, whereas in lenalidomide-insensitive HuT78 cells IKZF2 and IKZF3 remain unchanged and IKZF1 decreases but is still detectable.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of treating a cancer with lenalidomide in a subject, comprising:
   (a) obtaining a sample from the subject;
   (b) measuring mRNA level of cereblon (CRBN);
   (c) measuring mRNA level of IKZF1;
   (d) determining the ratio of the mRNA level of CRBN to the mRNA level of IKZF1; and
   (e) diagnosing the subject as being likely to be responsive to lenalidomide if the ratio of the mRNA level of CRBN to the mRNA level of IKZF1 is higher than 3;
   (f) administering lenalidomide to the subject diagnosed as being likely to be responsive to lenalidomide,
   wherein the cancer is an Adult T-cell Leukemia (ATL).

2. The method of claim 1, wherein the cancer is relapsed, refractory or resistant to conventional therapy.

3. The method of claim 1, wherein the method comprises diagnosing the subject as being likely to be responsive to lenalidomide if the ratio of the mRNA level of CRBN to the mRNA level of IKZF1 is higher than 4.

4. The method of claim 1, wherein the method comprises diagnosing the subject as being likely to be responsive to lenalidomide if the ratio of the mRNA level of CRBN to the mRNA level of IKZF1 is higher than 5.

* * * * *

UNITED STATES PATENT AND TRADEMARK OFFICE
CERTIFICATE OF CORRECTION

PATENT NO. : 10,338,077 B2  
APPLICATION NO. : 15/170789  
DATED : July 2, 2019  
INVENTOR(S) : Hidekatsu Iha et al.

Page 1 of 1

It is certified that error appears in the above-identified patent and that said Letters Patent is hereby corrected as shown below:

On the Title Page

Item (54) and in the Specification Column 1, Lines 1-4, "METHODS FOR DETERMINING DRUG EFFICACY FOR TREATMENT OF CANCER RATION OF CEREBLON ASSOCIATED PROTEINS," to read as -- METHODS FOR DETERMINING DRUG EFFICACY FOR TREATMENT OF CANCER USING RATIOS OF CEREBLON ASSOCIATED PROTEINS --

Signed and Sealed this  
Twelfth Day of November, 2019

Andrei Iancu  
*Director of the United States Patent and Trademark Office*